US012797484B2

(12) United States Patent
Hillaireau et al.

(10) Patent No.: US 12,797,484 B2
(45) Date of Patent: Nov. 17, 2026

(54) NANOPARTICLES OF ANTIRETROVIRAL DRUGS, THEIR PREPARATION AND THEIR USE FOR THE TREATMENT OF VIRAL INFECTIONS

(71) Applicants: CENTRE NATIONAL DE LA RECHERCHE SCIENTIFIQUE, Paris (FR); INSTITUT PASTEUR, Paris Dedex (FR); UNIVERSITE PARIS-SACLAY, Saint-Aubin (FR)

(72) Inventors: Hervé Hillaireau, Paris (FR); Elias Fattal, Paris (FR); Giovanna Giacalone, Paris (FR); Héla Saidi, Paris (FR); Marie-Lise Gougeon, Antony (FR); Marion Quaillet, Sainte-Geneviève-des-Bois (FR); Sarah Pallara, Saint-Joseph (FR)

(73) Assignees: CENTRE NATIONAL DE LA RECHERCHE SCIENTIFIQUE, Paris (FR); INSTITUT PASTEUR, Paris (FR); UNIVERSITE PARIS-SACLAY, Gif-sur-Yvette (FR)

( * ) Notice: Subject to any disclaimer, the term of this patent is extended or adjusted under 35 U.S.C. 154(b) by 692 days.

(21) Appl. No.: 17/294,149

(22) PCT Filed: Nov. 14, 2019

(86) PCT No.: PCT/EP2019/081301
§ 371 (c)(1),
(2) Date: May 14, 2021

(87) PCT Pub. No.: WO2020/099547
PCT Pub. Date: May 22, 2020

(65) Prior Publication Data

US 2022/0008554 A1 Jan. 13, 2022

(30) Foreign Application Priority Data

Nov. 16, 2018 (EP) .................................... 18306506

(51) Int. Cl.

| | |
|---|---|
| ***A61K 47/69*** | (2017.01) |
| ***A61K 9/00*** | (2006.01) |
| ***A61K 9/51*** | (2006.01) |
| ***A61K 31/4985*** | (2006.01) |
| ***A61K 31/505*** | (2006.01) |
| ***A61K 31/7072*** | (2006.01) |
| ***A61K 38/16*** | (2006.01) |
| ***A61K 47/52*** | (2017.01) |
| ***A61P 31/12*** | (2006.01) |

(52) U.S. Cl.
CPC ........ *A61K 47/6951* (2017.08); *A61K 9/0019* (2013.01); *A61K 9/5161* (2013.01); *A61K 31/4985* (2013.01); *A61K 31/505* (2013.01); *A61K 31/7072* (2013.01); *A61K 38/16* (2013.01); *A61K 47/52* (2017.08); *A61P 31/12* (2018.01)

(58) Field of Classification Search
None
See application file for complete search history.

(56) References Cited

U.S. PATENT DOCUMENTS

2012/0087859 A1 4/2012 Tae et al.
2015/0150981 A1* 6/2015 Gref .......................... C07F 3/06
514/777

FOREIGN PATENT DOCUMENTS

KR 20120059721 A * 6/2012 ............. A61K 47/36

OTHER PUBLICATIONS

Stanford Medicine "Risk of Exposure to HIV/AIDS" https://stanfordhealthcare.org/medical-conditions/sexual-and-reproductive-health/hiv-aids/causes/risk-of-exposure.html (accessed Dec. 19, 2023). (Year: 2023).*
CDC "PrEP Effectiveness" last reviewed Jun. 6, 2022, https://www.cdc.gov/hiv/basics/prep/prep-effectiveness.html (accessed Dec. 19, 2023) (Year: 2022).*
Baert et al. "Development of a long-acting injectable formulation with nanoparticles of rilpivirine (TMC278) for HIV treatment" European Journal of Pharmaceutics and Biopharmaceutics 2009, 72, 502-508 (Year: 2009).*
Giacalone et al. "Drug-Induced Nanocarrier Assembly as a Strategy for the Cellular Delivery of Nucleotides and Nucleotide Analogues" Biomacromolecules 2013, 14, 737-742 (Year: 2013).*
Parboosing et al. "Nanotechnology and the Treatment of HIV Infection" Viruses 2012, 4, 488-520 (Year: 2012).*
Giacalone et al. "Stabilization and cellular delivery of chitosan-polyphosphate nanoparticles by incorporation of iron" Journal of Controlled Release 2014, 194, 211-219 (Year: 2014).*
(Continued)

*Primary Examiner* — Bethany P Barham
*Assistant Examiner* — Judith Marie Kamm
(74) *Attorney, Agent, or Firm* — NIXON & VANDERHYE

(57) ABSTRACT

Nanoparticles comprising an antiretroviral drug such as AZT-TP or enfuvirtide encapsulated by a complex of chitosan and optionally a metal cation such as Fe3+, for use in treating or preventing HIV infection via subcutaneous or intramuscular administration. The nanoparticles have a size less than 300 nm and a high drug loading capacity between 20-60% by weight. They are prepared by mixing an aqueous solution of chitosan and metal cation with an aqueous solution of the drug. The chitosan-based nanoparticles provide an effective method to deliver antiretroviral drugs to key HIV reservoir sites with high drug loading and low toxicity.

5 Claims, 12 Drawing Sheets

(56) References Cited

OTHER PUBLICATIONS

Lalezari et al. "Influence of subcutaneous injection site on the steady-state pharmacokinetics of enfuvirtide (T-20) in HIV-1-infected patients" Journal of Clinical Virology 2003, 28, 217-222 (Year: 2003).*
International Search Report for PCT/EP2019/081301, mailed Jan. 8, 2020, 4 pages.
Written Opinion of the ISA for PCT/EP2019/081301, mailed Jan. 8, 2020, 9 pages.
Horcajada et al., "Porous metal-organic-framework nanoscale carriers as a potential platform for drug delivery and imaging", Nature Materials, vol. 9, No. 2, Feb. 1, 2010, pp. 172-178.
Giacalone et al., "Chitosan nanoparticles for the intracellular delivery of triphosphate nucleotide analogues", BMC Infections Diseases, vol. 14, No. Suppl 2, May 23, 2014, p. 75.
Giacalone et al., "Stabilization and cellular delivery of chitosan-polyphosphate nanoparticles by incorporation of", Journal of Controlled Release, vol. 194, Sep. 1, 2014, pp. 211-219.
Giacalone et al., "Drug-Induced Nanocarrier Assembly as a Strategy for the Cellular Delivery of Nucleotides and Nucleotide Analogues," Biomacromolecules 2013, vol. 14, pp. 737-742.
Wu et al., "Zinc-Stabilized Chitosan-Chondroitin Sulfate Nanocomplexes for HIV-1 Infection Inhibition Application," Mol. Pharmaceutics 2016, vol. 13, pp. 3279-3291.
Wu et al., "Zinc-stabilized colloidal polyelectrolyte complexes of chitosan/hyaluronan: a tool for the inhibition of HIV-1 infection," Journal of Materials Chemistry B, 2016, vol. 4, pp. 5455-5463.

* cited by examiner

A

| Type of CS-Fe | Critical N/P | AZT-TP Association efficiency (%) | Legend |
|---|---|---|---|
| CS-$Fe_{3\%}$ | 1.37 ± 0.11 | 40.9 ± 4.0 | |
| CS-$Fe_{6\%}$ | 1.46 ± 0.06 | 58.7 ± 1.7 | |
| CS-$Fe_{9\%}$ | 1.56 ± 0.08 | 62.9 ± 0.9 | |
| CS-$Fe_{12\%}$ | 2.15 ± 0.27 | 58.1 ± 6.1 | |

A – Infection of PHA – activated T cells

B – Infection of Macrophages
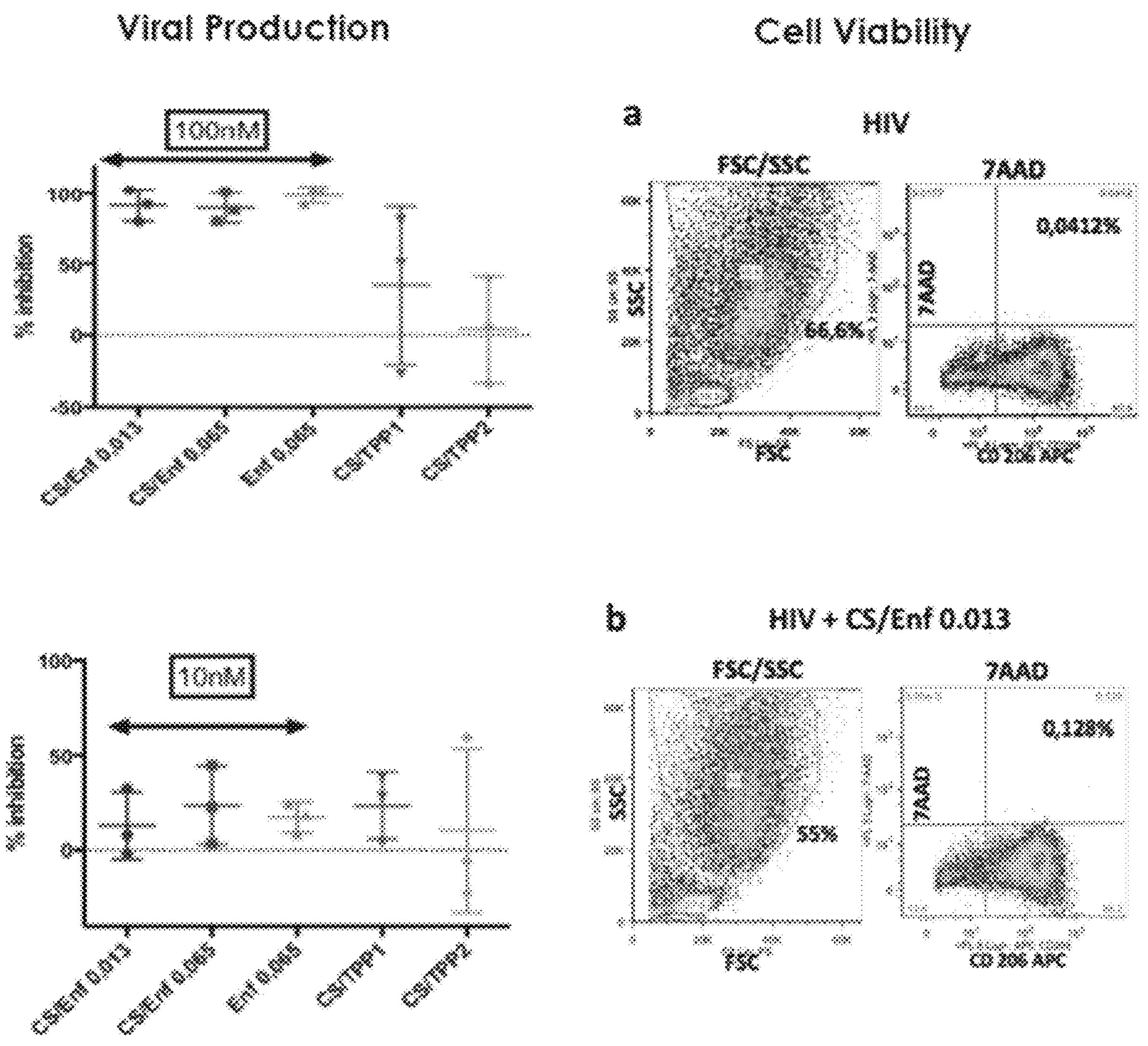
FIG.9 end

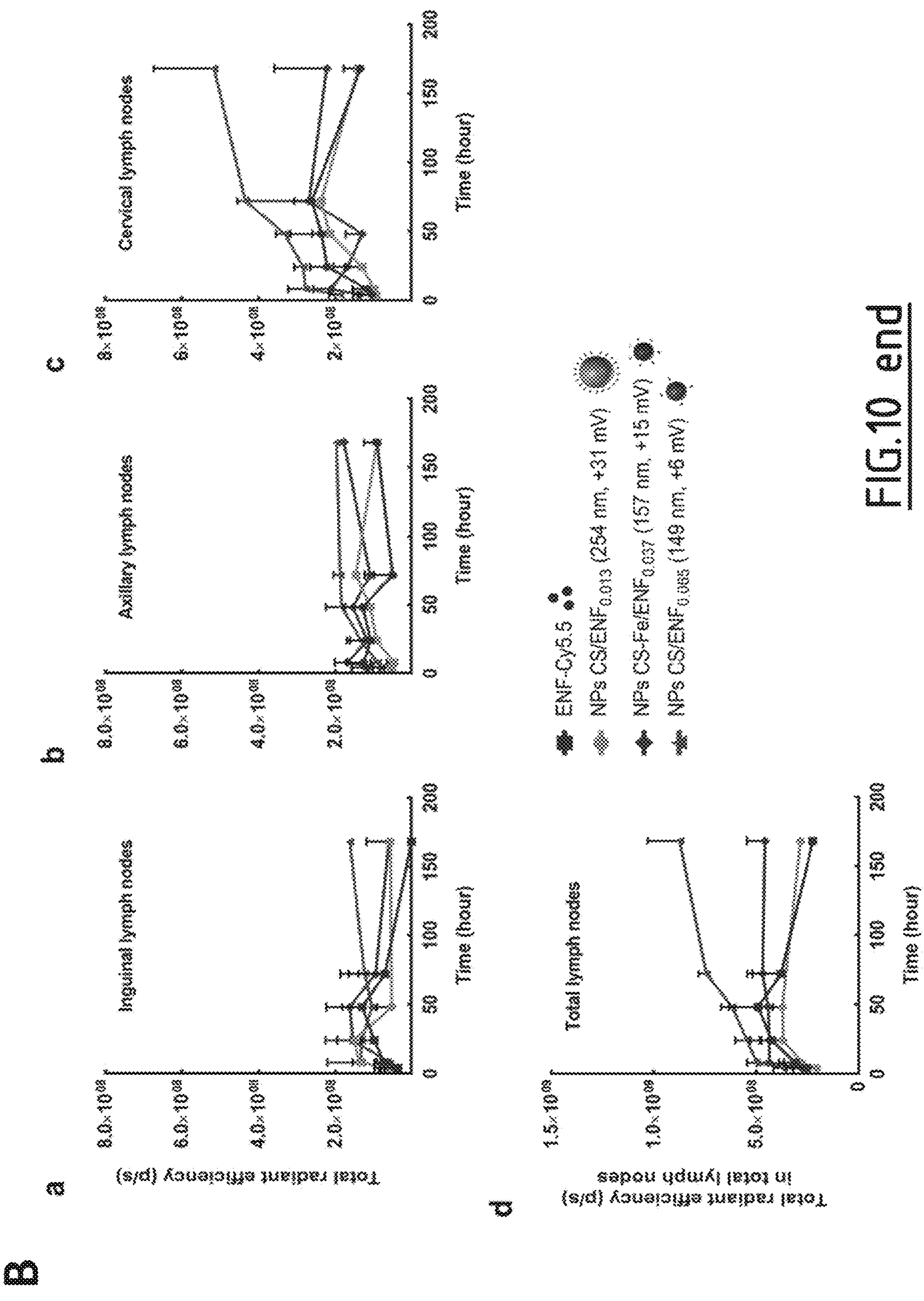
FIG. 10 end

NANOPARTICLES OF ANTIRETROVIRAL DRUGS, THEIR PREPARATION AND THEIR USE FOR THE TREATMENT OF VIRAL INFECTIONS

This application is the U.S. national phase of International Application No. PCT/EP2019/081301 filed 14 Nov. 2019, which designated the U.S. and claims priority to EP Patent Application No. 18306506.9 filed 16 Nov. 2018, the entire contents of each of which are hereby incorporated by reference.

BACKGROUND OF THE INVENTION

Description of the Related Art

Nucleoside reverse transcriptase inhibitors (NRTIs) were the first drugs discovered and introduced in the treatment of HIV/AIDS. They remain a cornerstone of current highly active antiretroviral therapy (HAART) in association with protease inhibitors (PI) and non-nucleoside reverse transcriptase inhibitor (NRTI). It is indeed important to include in the therapy a drug that can act at the viral DNA synthesis level by competing with natural nucleosides, in order to target the virus at its different stages. Among the NRTIs, zidovudine (AZT) was the first drug introduced in the anti-HIV therapy, and therefore the one with most clinical data available.

Nevertheless, NRTIs present two main limitations. First, like many drugs, their biodistribution lacks specificity. This can be due to several reasons such as the physicochemical properties of the molecules, protein-binding or metabolization. The concentration of antiretroviral drugs is considerably lower in viral reservoirs like macrophages or viral sanctuaries like lymph nodes.

The second drawback of this class of drugs is their limited intracellular activation. Once in the cell cytoplasm, NRTIs need to be triphosphorylated by cellular kinases into their active form. However this conversion can be limited by the poor recognition between the enzymes and the drug, leading to very low portions of the administered drug being in its active form. The administration of the active triphosphate form of NRTIs would bypass this bottleneck, but this approach is made difficult by the chemical instability of the molecule in the physiological environment, and its poor penetration through membranes due to its hydrophilic and charged character. In order to make this strategy possible, there is the need of protecting the molecule and facilitating its membrane crossing.

A solution to this double difficulty was provided by the application of nanotechnology. On the one hand, in order to deliver NRTIs to reservoirs and sanctuaries, polyalkylcyanoacrylate nanoparticles and liposomes have been reported as nanocarriers of AZT to the organs of the mononuclear phagocyte system. Few studies report the encapsulation of triphosphate forms of NRTIs such as AZT-TP in nanocarriers (PEI nanogels, PIBCA nanoparticles or iron carboxylates metal-organic frameworks) in order to protect the triphosphate molecule and enable in vitro its uptake by cells. However, few attempts have been made addressing these two challenges, i.e. delivering triphosphate forms of NRTIs in vivo to the mononuclear phagocyte system.

Enfuvirtide is another antiretroviral drug, of the class of the HIV fusion inhibitors. Its use is however limited due to its peptide structure which makes it poorly soluble in physiological conditions and requires a subcutaneous administration, several times a day.

The cationic surface of chitosan is expected to contribute to its superior targeting efficacy to negatively charged cells. Interestingly, the choice of chitosan based nanoparticles for the design of a novel drug delivery system is due to their hydrophilic character that facilitates the administration of poorly absorbable drugs across various epithelial barriers. Moreover, the polycationic nature of chitosan is expected to favor deposition of the complement proteins on the nanoparticles, resulting in their better uptake by the macrophages trough complement receptors. Since macrophages serve as HIV-1 reservoirs, efficient drug delivery to these cells via chitosan could be an advantage. T cells and dendritic cells (DCs) constitute additional HIV-1 reservoirs. Notably, virus transfer from dendritic cells to T cells was shown to sustain viral persistence.

Giacalone et al Biomacromolecules 2013, 14, 737-742 reported the synthesis of nanoparticles of chitosan and AZT-TP.

Giacalone et al. *J. Control Release,* 2014, 194, 211-219 also disclosed the stabilization and cellular delivery of chitosan-polyphosphate nanoparticles by incorporation of iron. Wu et al. Journal of materials chemistry B 2016, 4, 5455-5463 reported $Zn^{2+}$ stabilized nano-complexes of chitosan/hyaluronan for the delivery of tenofovir. Wu et al Molecular pharmaceutics 2016, 13, 3279-3291 reported $Zn^{2+}$ stabilized chitosan-chondroitin sulfate nanocomplexes for encapsulating tenofovir.

However, the complexes are intended for oral administration.

Investigations have been carried out to improve the delivery of anti-retroviral drugs, including to increase the loading of the drug into the nanocarriers, and the control of the drug release.

In order to target the HIV reservoirs, such as lymph nodes, improved delivery systems and/or routes of administration are still required.

SUMMARY OF THE INVENTION

The present invention provides the preparation of nanoparticles assembly of chitosan with an high anti-retroviral drug, with a high drug load, efficient cellular delivery and intake, achieving high accumulation of the drug in lymph nodes.

According to a first object, the present invention concerns a nanoparticle comprising an antiretroviral drug encapsulated by an encapsulation complex, said complex comprising chitosan and optionally one or more metal cation, for use for treating and/or preventing viral infections, such as HIV and/or the symptoms thereof, where said use comprises administering said nanoparticle by the sub-cutaneous or intramuscular route.

As used herein, nanoparticle is a nano object with all three external dimensions in the nanoscale, and refers to particles between 1 and 1000 nm, preferably 1 to 500 nm, still preferably 1 to 200 nm in maximum size Typically, administration will be achieved by means of an aqueous suspension of said nanoparticles.

According to a further object, the present invention also concerns an aqueous suspension of said nanoparticles for use for treating and/or preventing viral infections, such as HIV and/or the symptoms thereof, where said use comprises administering said aqueous suspension by the sub-cutaneous or intramuscular route.

The pH of the suspension may be close to physiological pH, approximately comprised between 7 and 7.5.

According to an embodiment, said antiretroviral drug may be chosen from known antiretroviral drugs, and in particular may be chosen from the group consisting in AZT-TP, enfuvirtide, cabotegravir, rilpivirine, tenofovir or pharmaceutically acceptable salts thereof.

Typically, AZT-TP and enfuvirtide may be cited.

AZT (azidothymidine) or zidovudine is an antiretroviral drug used to treat HIV/AIDS. AZT-TP is its active triphosphate form that can display antiviral activity by interfering with viral nucleic acid synthesis. The clinical use of AZT-TP is however limited due to the presence of a triphosphate group which is prone to hydrolysis in vivo and responsible for the high hydrophilicity of the molecule, thereby strongly limiting its uptake by targeted cells and access to its intracellular target.

However, when assembled with chitosan and one or more metal ions into nanoparticles according to the invention, such nanoparticles were shown to be able to deliver AZT-TP to murine and human macrophages, to exert antiviral activity on HIV-infected primary human T cells, macrophages and DCs, and to lead in vivo to AZT-TP accumulation in lymph nodes after subcutaneous administration to mice.

Enfuvirtide is an HIV fusion inhibitor, the first of a novel class of antiretroviral drugs used in combination therapies for the treatment of HIV-1 infection and marketed under the trade name Fuzeon (Roche). It is an effective alternative for the management of the infection in case of virologic failure, but its peptide nature (36 amino-acids) limits its stability in physiological conditions, thus requiring twice daily subcutaneous administrations to patients.

This is a major limitation to the use of this antiretroviral class, in addition to the lack of accessibility of antiretroviral molecules in general to viral reservoirs/sanctuaries (eg. lymph nodes), which is one of the identified obstacles towards "HIV cure". According to the invention, chitosan and chitosan-metal-based nanogels are nanocarriers aimed at improving the antiretroviral drug delivery. In particular, the nanogel formulation of the invention has been shown to control the drug loading and nanogel stability. The nanocarriers of the invention allow to improve cellular delivery of the drug (in particular on human macrophages and lymphocytes), as well as its antiviral efficacy. They also allow to target lymph nodes following subcutaneous or intramuscular administration.

According to an embodiment, said antiretroviral drug is AZT-TP and said encapsulation complex comprises chitosan and one or more metal cation.

In particular, said metal cation may be $Fe^{3+}$, $Zn^{2+}$, $Fe^{2+}$.

According to an embodiment, when the nanoparticle includes a metal cation, the said nanoparticle comprises from about 1 to about 20% of said metal (in weight) with respect to the weight of the chitosan/metal complex.

Some nanoparticles are novel per se and are also part of the invention.

According to a further object, the present invention concerns a nanoparticle comprising an antiretroviral drug encapsulated by an encapsulation complex, said complex comprising chitosan and $Fe^{3+}$, preferably from 1 to 20% of Fe in weight with respect to the weight of the chitosan/Fe complex.

According to an embodiment, said antiretroviral drug is AZT-TP or enfuvirtide, preferably AZT-TP.

According to a further object, the present invention also concerns a nanoparticle comprising enfuvirtide encapsulated by an encapsulation complex, said complex comprising chitosan, and optionally one or more metal cation, such as $Fe^{3+}$.

According to the various objects of the invention, the nanoparticles generally have a mean diameter (in number or in intensity) of less than 300 nm.

Their content in the antiretroviral drug (drug loading) is generally comprised between 20 to 60% of antiretroviral drug in weight with respect to the total weight of the nanoparticle.

According to an embodiment, the nanoparticles may be characterized by their molar ratio between the drug and amino group of chitosan. As used herein, the "critical ratio" illustrates the molar ratio between the molar content of the drug respective to the molar content of chitosan in the nanoparticles, at which visible aggregation occurs during the nanoparticle formation. The critical ratio thus corresponds to the maximum ratio of the amount of the drug in the nanoparticle relative to the amount of the chitosan in the nanoparticle. The critical ratio may depend on the pH of the suspension, the chitosan concentration, the pH of the drug solution, etc. It is generally comprised between 0.03 and 0.3 (mole of drug per mole of chitosan unit), corresponding to a maximal drug content of the nanoparticles of 59.9% (g of drug per g of nanoparticle).

According to a further object, the present invention also concerns the process of preparation of a nanoparticle of the invention, said process comprising mixing a S1 aqueous solution of chitosan and an optional metal cation, together with a S2 aqueous solution of said antiretroviral drug.

Typically, the pH of the S1 solution is comprised between 4 and 7.5, more typically between 5 and 6. Typically, the pH of the S2 solution is comprised between 4 and 11. The pH may be adjusted by using appropriate buffer, as necessary. The concentration of chitosan in the S1 solution is generally comprised between 0.3 and 1 mg/ml.

According to a further object, the present invention also concerns a pharmaceutical composition comprising a nanoparticle of the invention.

Said pharmaceutical composition is generally in the form of an aqueous solution, suitable for subcutaneous or intramuscular injection. In particular, the injection may be carried out at the site of the viral reservoirs, such as lymph nodes.

The composition may comprise one or more pharmaceutically acceptable excipients.

According to a further object, the present invention also concerns the nanoparticle for use for treating and/or preventing viral infections, such as HIV and/or the symptoms thereof.

According to a further object, the present invention also concerns a nanoparticle for use according to the invention, wherein said nanoparticle is administered in combination with one or more antiretroviral drug(s). Said administration may be separate, simultaneous or staggered over time.

It is also disclosed a method for treating and/or preventing viral infections, by administering to a patient in the need thereof a therapeutically effective amount of nanoparticles or of a pharmaceutical composition according to the invention.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, "pharmaceutically acceptable salts" refer to derivatives of the disclosed drugs wherein the parent drug is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids and the salts prepared from organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* $17^{th}$ ed., Mack Publishing Company, Easton, PA, 1985, p. 1418, the disclosure of which is hereby incorporated by reference.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of the nanoparticles or pharmaceutical composition of the invention which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

In general terms, the compounds of this invention may be provided in an aqueous physiological buffer solution containing 0.1 to 1% w/v compound. Typical dose ranges are from 1 μg/kg to 0.1 g/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Nanoparticles provided herein can be formulated into pharmaceutical compositions by admixture with water and/or one or more pharmaceutically acceptable excipients. Such compositions may be prepared for use in various administration routes, such as oral (particularly in the form of tablets or capsules); or parenteral administration (particularly in the form of liquid solutions, suspensions or emulsions). The subcutaneous and intramuscular routes are preferred.

The compositions may conveniently be administered in unit dosage form and may be prepared by any of the methods well known in the pharmaceutical art, for example, as described in Remington: *The Science and Practice of Pharmacy,* $20^{th}$ ed.; Gennaro, A. R., Ed.; Lippincott Williams & Wilkins: Philadelphia, PA, 2000. Pharmaceutically compatible binding agents and/or adjuvant materials can be included as part of the composition. Oral compositions will generally include an inert diluent carrier or an edible carrier.

Liquid preparations for administration include sterile solutions, suspensions, and emulsions. They may be aqueous or non-aqueous, although aqueous solutions are particularly preferred. The liquid compositions may also include binders, buffers, preservatives, chelating agents, and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Figure 1:
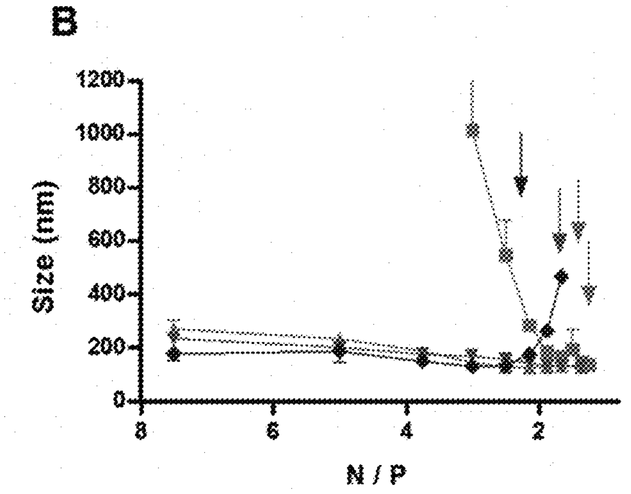
FIG. 1 illustrates the nanoparticle formation from various CS—Fe complexes and AZT-TP. (a) Critical N/P ratios of nanoparticle aggregation from various CS—Fe complexes, and corresponding AZT-TP association efficiency at the critical N/P. (b) Size, (c) polydispersity index and (d) zeta potential of AZT-TP/CS—Fe formulations as a function of the N/P ratio. Arrows on (b), (c) and (d) indicate the critical N/P ratio for each CS—Fe complex.
Figure 1:
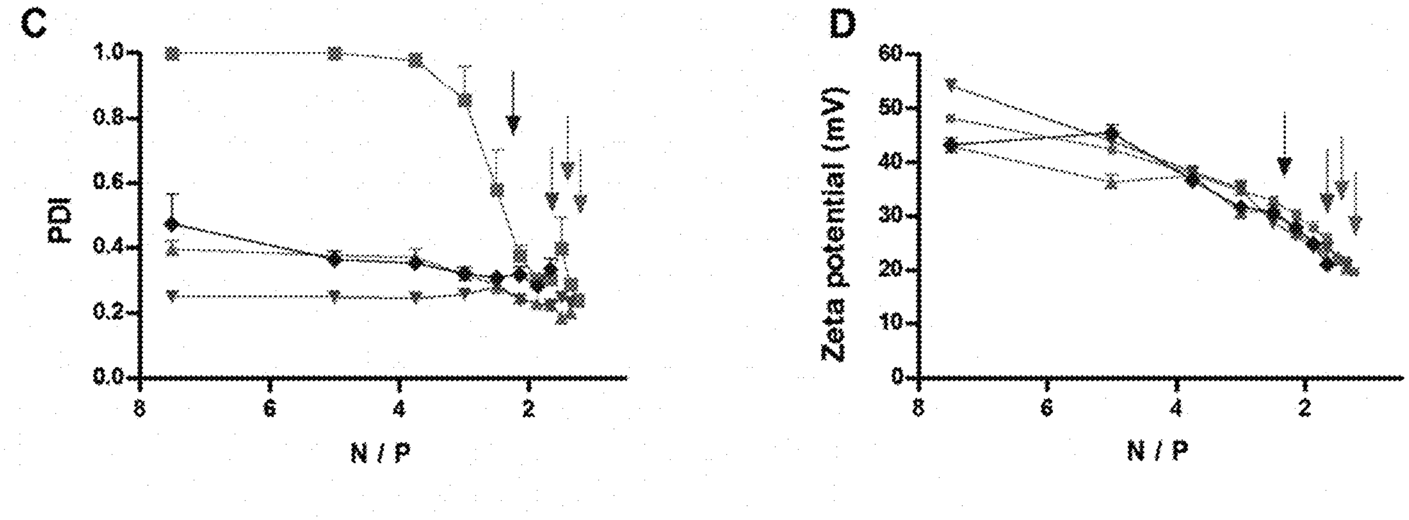

(A): PBMC from healthy donors were stimulated for 6 days with PHA (0.5 μg/ml) and IL-2 (1 μg/ml), and incubated for 1.5 h at 37° C. with HIV-$1_{BAL}$ (1 ng/ml of p24), pre-treated or not for 1 h at 37° C. with the nanoparticles (CS/Enf 0.013, CS/Enf 0.065), or Enf 0.065, or their controls (CS/TPP1, CS/TPP2) at indicated concentrations (1-100 nM). The cells were then centrifuged and further incubated for 6 days in complete medium in the presence of the same compounds. Viral production was assessed by the quantification of p24 in culture supernatants. Results are expressed as % of inhibition of p24 production (left hand-side). Data from one representative experiment out of 4 independent experiments are shown. Cell viability was assessed in the same cultures using multiparametric flow cytometry following constraining of the cells with anti-CD3, -CD4, -CD8 mAbs and 7-AAD (right handside). An example of fluorescence analysis is shown on the dot plots: gated CD3+ T cells were analyzed for CD4 and CD8 markers and the % of 7AAD+ cells was calculated in CD4 T cells. This method was used in uninfected and HIV-infected T cells, and the data show the lack of toxicity of nanoparticles in both uninfected and infected cells, thus showing that the inhibition of viral replication by nanoparticles was not due to the death of infected cells.

(B): Monocytes were isolated from PBMC by a positive selection with CD14-beads, and further differentiated into macrophages following 6 days of treatment with M-CSF. Macrophages were incubated for 1.5 h at 37° C. with HIV-$1_{BAL}$ (1 ng/ml of p24), pre-treated or not for 1 h at 37° C. with the nanoparticles (CS/Enf 0.013, CS/Enf 0.065), or Enf 0.065, or their controls (CS/TPP1, CS/TPP2) at indicated concentrations (1-100 nM). The cells were then centrifuged and further incubated for 3 days in complete medium in the presence of the same compounds. Viral production was assessed by the quantification of p24 in culture supernatants. Data from 3 independent experiments are shown for 2 concentrations of nanoparticles (10 nM and 100 nM). Mean±SD are shown. Cell viability, assessed with the 7AAD dye which stains dead cells shows no toxicity of the virus and the virus combined with nanoparticles in CD206+ cells, a specific marker of macrophages.

Figure 10:
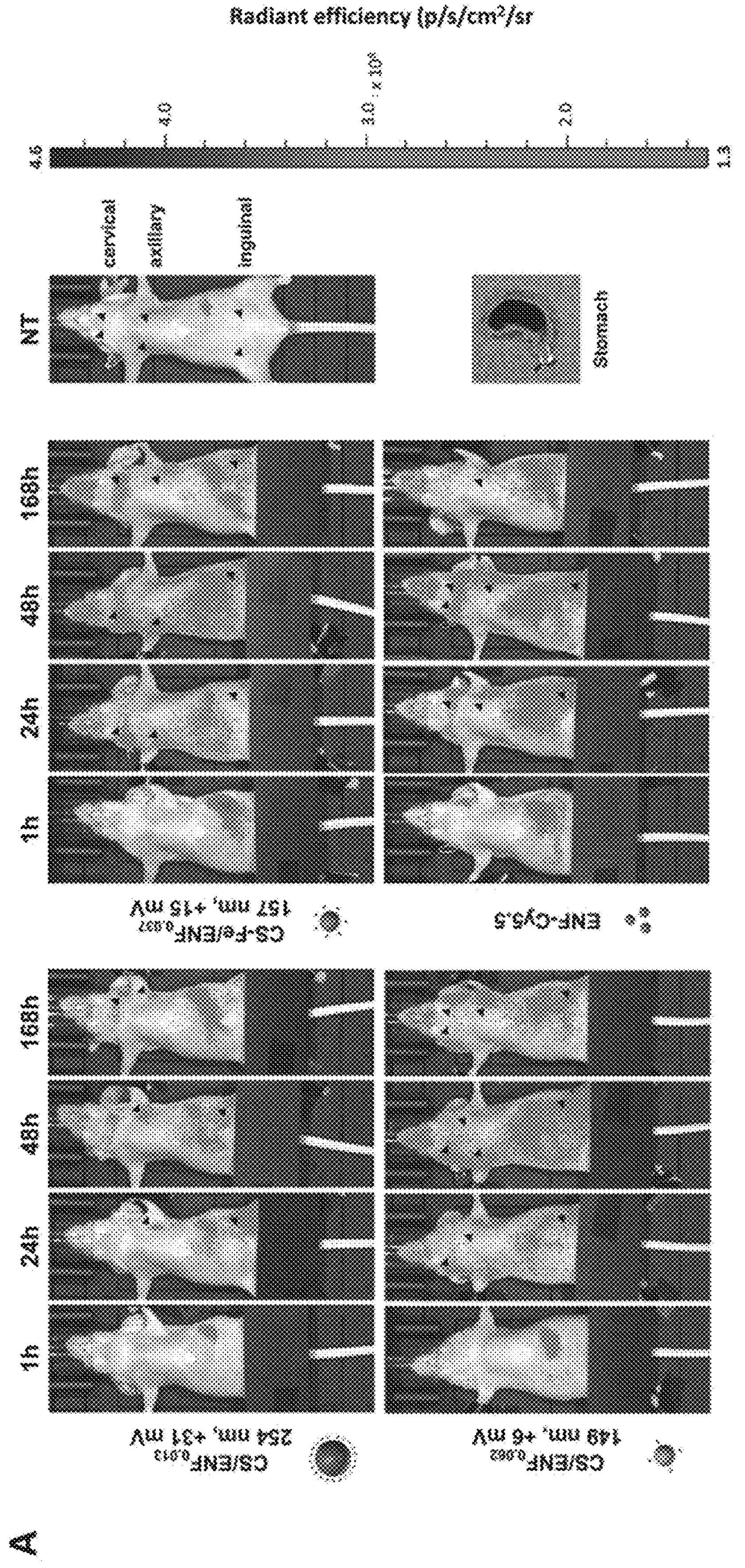

FIG. 10 illustrates the in vivo fate of Enfuvirtide delivered as CS/Enf nanoparticles following subcutaneous administration, showing an accumulation of enfuvirtide in lymph nodes.

DESCRIPTION OF THE PREFERRED EMBODIMENTS

Example 1: Nanoparticles of AZT-TP

1. Tests

1. Nanoparticle Preparation

CS—Fe complexes were first prepared as described (Giacalone et al *J Control Release,* 2014, 194, 211-219). Briefly, iron nitrate (Sigma) was dissolved in water with chitosan (low viscosity, 95% deacetylated, Fluka) (10 mg/mL, pH=1.5) and the complex was allowed to form overnight under mechanical stirring. The complex was washed from free iron through the precipitation with acetone, until the filtrate was completely free from iron. CS—Fe was then dried paying attention to the formation of films which should be avoided. Different complexation conditions were used in order to achieve different degrees of binding between chitosan and iron (CS-$Fe_{3\%}$ 0.5 M iron nitrate, CS-$Fe_{6\%}$ 0.1 M iron nitrate, CS-$Fe_{9\%}$ 0.1 M iron nitrate stirring 2 days, CS-$Fe_{12\%}$ smaller scale). Nanoparticle formation was then assessed by slow addition of a 27 mM AZT-TP (Chemcyte, Inc., San Diego, USA) solution to a 1 mg/mL CS—Fe solution under magnetic stirring (1000 rpm). For radioactivity studies, AZT-TP nanoparticles were formed from a 27 mM AZT-TP solution prepared using [methyl-$^3$H]-AZT-TP (Perkin Elmer, France) as a tracer, by diluting the commercial 10 mCi/mL (25 mM) with appropriate amount of unlabelled AZT-TP solution.

For in vitro studies, nanoparticles were prepared by adding a 27 mM AZT-TP solution to 3 mL of CS—Fe under magnetic stirring. They have been purified from free AZT-TP and CS by centrifugation at 750×g on a glycerol bed, the supernatant has been discharged and the pellet has been re-suspended. For storage purposes, nanoparticles have been freeze-dried by adding trehalose at the final 10% w/v concentration. The suspension has been frozen in liquid nitrogen and freeze-dried at −55° C. and 0.01 mbar for 24 hours using a Christ Alpha 1-2 LD Plus.

2. Nanoparticle Characterization

The mean size of nanoparticles was determined using photon correlation spectroscopy (PCS), with a 173° scattering angle at a temperature of 25° C., and their zeta potential was determined after 1/20 sample dilution in 1 mM NaCl solution, using a Zetasizer MAL 500180 (Malvern Instrument, UK).

In order to determine the amount of AZT-TP associated to the nanoparticles, their composition was studied using [methyl-$^3$H]-AZT-TP (final concentration 1 μCi/mL). Nanoparticles were prepared as described above using 4 different CS—Fe complexes. They were centrifuged at 17000×g for 1 hour in order to separate them from free AZT-TP. Both pellets and supernatants were then analyzed to determine their radioactivity content using a Beckman Coulter instrument (LS 6500 Multi-Purpose Scintillation Counter). The AZT-TP association efficiency was calculated as the ratio of the pellet radioactivity to the total (pellet+supernatant) radioactivity. The drug loading of nanoparticles was expressed as the ratio of the nanoparticle-associated drug weight to the nanoparticle (drug+CS) weight.

3. Cell Culture and Viability Assessment on Non-Infected Cells

J774A.1 mouse macrophages (from ECACC, catalogue number 91051511) and THP-1 human acute monocytic leukemia cells (from ATCC, catalogue number TIB-202) were grown in RPMI 1640 medium (BE 12-702 F, Lonza) supplemented with 10% (v/v) fetal bovine serum (Lonza) (heat-inactivated in the case of J774.A1), penicillin (100 UI/mL) and streptomycin (100 μg/mL). Cells were maintained in a humidified incubator with 95% air/5% $CO_2$ at 37° C. Cells were used from passage 3 to 20 (J774A.1) or 12 (THP-1) after thawing. THP-1-derived macrophages were obtained by incubation of THP-1 monocytes with $10^{-8}$ M phorbol 12-myristate 13-acetate (PMA) for 24 hours and subsequent incubation with fresh medium, before running the experiment.

The cytotoxicity of nanoparticles towards both cell lines was determined using an MTT assay (Mosmann et al *J Immunol Methods,* 1983, 65, 55-63). Cells were recovered from flasks, counted with Neubauer chamber and diluted to needed concentration, to be seeded in a 96-well plate at a density of 30,000 cells/well for J774A.1 and 60,000 for THP-1. They were pre-incubated for 24 hours. Nanoparticles were prepared and purified, diluted at different concentrations in cell culture medium and then incubated with cells for 24 h. Supernatants were then withdrawn and a solution of 0.5 mg/mL MTT in medium was added. After 2 h incubation, supernatant was removed and DMSO was added to dissolve formazan crystals. Plates were stirred a few minutes and absorbance measurement were run at λ=570 nm, using a Labsystems Multiskan MS plate reader. The cytotoxicity of CS—Fe solutions at a concentration equivalent to the highest nanoparticle concentration was determined as well for comparison.

4. Cellular Uptake Studies

Nanoparticles containing [methyl-$^3$H]-AZT-TP were prepared and purified as described above then diluted 1:10 in cell culture medium (in order to maintain cell viability above 80% as determined by MTT tests), so to have 70 nCi/well. A control solution of AZT-TP at the same final radioactivity concentration was used for comparison.

Cells were recovered from the culture flasks, counted and seeded in 6-well plates, at a surface density of 800,000 cells/well for J774A.1 and 160,000 for THP-1 using 2 mL medium per well. After 24 h incubation, the medium was withdrawn and 2 mL of AZT-TP nanoparticles or free AZT-TP were added in each well. Nanoparticles and AZT-TP were incubated with cells for 2 and 8 hours, after which the uptake was stopped by removing the cell culture medium. The cells were washed twice with PBS (Lonza) to remove loosely bound compounds and then lysed with 1 mL Solvable (Perkin-Elmer, France). The radioactivity of the supernatant medium, the washing supernatants and the cell lysate were counted. The uptake kinetics of nanoparticle AZT-TP was studied for 2 and 8 hours and compared to that of free AZT-TP.

5. Production of HIV Viral Stock

CCR5-tropic HIV-1 Ba-L was amplified in Peripheral Blood Mononuclear Cells (PBMCs) of healthy donors. HIV-1 concentration was quantified in cell culture supernatants by means of the DuPont HIV-p24 antigen ELISA (HIV-1 core profile ELISA; DuPont de Nemours, Les Ulis, France). For screening experiments, a volume of PV stock diluted to a concentration ultimately resulting in a signal of $1\times10^5$ RLU was used [25].

6. In Vitro Differentiation of Monocyte-Derived Dendritic Cells (DCs) and Macrophages PBMCs were separated from the blood of healthy adult donors on a Ficoll-Hypaque density gradient. Blood was obtained through the EFS (Establishment Francais du Sang) in the setting of EFS-Institut Pasteur Convention. A written informed consent was obtained for each donor to use the cells for clinical research according to French laws. Our study was approved by IRB, external (EFS Board) as required by French law and internal (Biomedical Research Committee Board, Institut Pasteur). Monocytes were isolated from fresh PBMCs using the Monocyte Negative Isolation Kit (StemCell Technologies) according to the manufacturer's protocol. The enriched cells were assessed for more than 90% purity using the following antibodies: anti-CD14-FITC (Miltenyi Biotec) and anti-CD3-APC (Becton Dickinson-Pharmingen). Monocytes were differentiated to dendritic cells using 10 ng/ml rhGM-CSF (Peprotech) in combination with rhIL-4 (10 ng/ml). Macrophages were differentiated from monocytes using 10 ng/ml of rhM-CSF (Peprotech). After 6 days of culture, flow cytometry analysis demonstrated that CD14neg DC-SIGN+DCs and CD209+ macrophages were more than 90% pure.

7. Purification of Autologous T Lymphocytes

Peripheral blood lymphocytes (PBL) were subsequently prepared from the monocyte-depleted fraction (>90% CD3+ T cells and <1% monocytes, as assessed by flow cytometry). PBL were stimulated for 48 hours in fresh medium supplemented with PHA (2.5 μg/ml) and rhIL-2 (1 μg/ml) and were further cultured with rhIL-2 (1 μg/ml) for 24 hours.

8. HIV-1 Entry into Primary Cells

In this series of experiments, CS-$Fe_{12\%}$/TPP (Sigma) nanoparticles have been prepared as well as a control ("empty nanoparticles", E-NP). These nanoparticles are similar to CS-$Fe_{12\%}$/AZT-TP in terms of size and composition. They only differ in that AZT-TP is replaced by the inactive triphosphate moiety of AZT-TP (i.e. tripolyphosphate, TPP). CS-$Fe_{12\%}$/TPP nanoparticles are purified and freeze-dried in a similar way as described for AZT-TP nanoparticles. As controls, AZT and AZT-TP solutions at corresponding concentrations have been prepared as well. To assess the entry of HIV-1 into T cells, macrophages and DCs, the cells were washed twice after 6 days of activation/differentiation and seeded into 96-well culture plates ($1\times10^5$ cells/well). HIV-1 (1 ng p24 antigen) and increasing doses of the molecules to be tested were added on indicated cell subsets in triplicate and incubated for 1 h at 37° C. in a 5% $CO_2$ atmosphere. After 4 washes to remove the unattached virus, cells were lysed by incubation for 45 min at 37° C. with 1% Triton X-100. Cell lysates were harvested and centrifuged at 1,800 rpm for 5 min. The amount of cell-associated HIV-1 was evaluated using the p24 antigen capture ELISA.

9. Inhibition of HIV-1 Infection in T Cells or Macrophages

After 6 days of activation or differentiation, cells were washed twice and seeded into 96-well culture plates ($25\times10^5$ cells/well). HIV-1 (1 ng p24 antigen/ml) and increasing concentrations of molecules to be tested were added on indicated cell subsets in triplicate and incubated for 3 h at 37° C. in a 5% $CO_2$ atmosphere. After 4 washes to remove exceeding virus, cells were cultured for 6 days. The level of virus replication was monitored by HIV-1 p24 antigen ELISA. Supernatants were harvested and virus particles were lysed by incubation for 45 min at 37° C. with 1% Triton X-100.

10. DCs-Mediated Infection of Autologous T Cells

To assess the transmission of HIV-1 from DCs to autologous T-cells, DCs were incubated into 96-well culture plates ($1\times10^5$ cells/well) and infected with HIV-1 (1 ng p24 antigen) for 3 h at 37° C. in a 5% $CO_2$ atmosphere. Following four washes, DCs were shortly incubated with increasing concentrations of indicated molecules or AZT (2 μM), and autologous stimulated T cells were added onto HIV-exposed DCs at DC:T-cell ratio of 1:5. Cells were cultured for 6 days. Each sample was performed in triplicate. Culture supernatants were harvested every 3 days and fresh medium with compounds was added. Supernatants were inactivated with 1% Triton X-100 and frozen at −20° C. Viral production by T lymphocytes was evaluated at the sixth day of the co-culture by measurement of p24 antigen in supernatants using capture ELISA.

11. Quantification of the Frequency of Infected Cells

Following six days of infection, the frequency of HIV-1-infected cells was determined by flow cytometry to detect intracellular HIV-1 p24 molecule. Cells were surface-stained with antibodies specific for CD3 (BD Biosciences, San Jose, CA) to target T cells or CD206, HLA-DR and CCR5 (BD Biosciences, San Jose, CA) to target macrophages, and intracellularly stained with p24-specific antibody (Coulter). Stained cells were immediately acquired on a FACScalibur (Becton Dickinson) and analyzed with FlowJo software.

12. Apoptosis Measurement

Cell survival was determined with the 7-AAD assay, as described previously [26]. Briefly, cultured cells were stained with 20 μg/mL nuclear dye 7-amino-actinomycin D (7-AAD; Sigma-Aldrich) for 30 minutes at 4° C. Surviving cells were identified as 7-$AAD^{neg}$.

13. Animals 6- to 8-week-old NIH Swiss Outbred female mice were purchased from Harlan Laboratory (UK). All animals were housed in appropriate animal care facilities during the experimental period, with free access to food and water, and were handled according to the principles of laboratory animal care and legislation in practice in France. All in vivo studies were performed in accordance with a protocol submitted to the local Ethical Committee (registered with the French Ministry of Research).

14. Subcutaneous Administration and Dosage in Lymph Nodes

The systemic toxicity of the tested nanoparticles was first investigated and compared to those of free AZT-TP and CS-$Fe_{12\%}$ complex after single injection into the hock of healthy mice. Noteworthy, the injected dose of nanoparticles containing AZT-TP was limited by the maximum concentration of nanoparticles possible in suspension and the maximum volume able to be injected, both corresponding to an AZT-TP equivalent dose of 1.3 mg/kg. Whatever the dosing protocol, any toxicity of tested nanoparticles was observed. We therefore used this protocol to evaluate the nanoparticle biodistribution in mice. Practically, 1 mM [methyl-$^3$H]-AZT-TP solution and [methyl-$^3$H]-AZT-TP nanoparticle suspension at the corresponding AZT-TP concentration were prepared as described above. Both formulations were prepared at 20 μCi/mL and each mouse received 50 μL, i.e. 1 μCi. For all the injections, a 26-gauge needle was used. 10 minutes before administrations, mice were anesthetized with an intraperitoneal injection of a mixture 10:1 of ketamine/xylazine at 90 mg/kg. The mice were randomly divided into 2 groups of 12 each and all groups received a single injection into the hock with either (i) [methyl-$^3$H]-AZT-TP solution or (ii) nanoparticles containing [methyl-$^3$H]-AZT-TP. The injected volume was 50 μL. 2 or 4 hours after injection into the hock, mice (n=6 at each time point) were sacrificed and inguinal and axillary right and left lymph nodes were collected. Samples were then dissolved by addition of 1 ml of Solvable and overnight incubation at 50° C. Subsequently, they were bleached using hydrogen peroxide (30% w/w, Sigma) and their radioactivity content was determined by scintillation counting. Statistical analyses were performed using T-test and Two-way ANOVA test.

To visualize the lymph nodes, mice were anesthetized with 2.5% isoflurane, and dye (i.e., blue trypan, 0.4%) was injected subcutaneously into the inguinal right lymph node, with the needle pointed in a rostral direction. The injection site should bleb lightly, before the dye is slowly taken up by lymphatic vessels. After 5 to 15 minutes of continuous anesthesia to allow the dye to travel through lymphatics, mice were euthanized with 002. The blue-labeled inguinal and axillary lymph nodes were easily located and imaged.

15. Statistical Analysis

The non-parametric Wilcoxon signed-rank and T-test were used for statistical analysis of in vitro studies. A $p\text{-value}<0.05$ was considered significant. The two-way ANOVA and the T-test were used for statistical analysis of in vivo studies.

2. Results

1. Nanoparticle Formation from CS—Fe and AZT-TP

The formation of nanoparticles from CS—Fe complexes and AZT-TP has been investigated at various ratios between the two components, expressed as N/P (N: nitrogen concentration in chitosan solutions; P: phosphorus concentration in AZT-TP solutions). Four CS—Fe complexes have been used, containing respectively 3, 6, 9 and 12% of iron out of the total mass of the complex. For all formulations, the nanoparticle formation region was determined as occurring above a critical N/P ratio, this ratio corresponding to the N/P value at which visible aggregation occurs. The critical N/P was found to be in the range of 1.4-2.2 depending on the type of CS—Fe complex (FIG. 1A), with the following trend: the more the iron in the CS—Fe complex, the higher the critical N/P. A possible explanation is that the increased presence of iron on the amine sites of chitosan might at some extent limit the access to the phosphate groups for complexation, therefore leading to aggregation at higher N/P.

All formulations have been further characterized in terms of particle size and polydispersity (PCS) as well as surface charge (zeta potential). The critical N/P ratios were confirmed by PCS measurements, showing a decrease in size until a minimal value around 150 nm is reached, before increasing again due to aggregation (FIG. 1B). The polydispersity index follows the same trend, decreasing down to around 0.2 at the critical N/P, and increasing again following nanoparticle aggregation (FIG. 1C). Zeta potential is positive as expected because of chitosan charges, and it also decreases consistently with the complexation of the positive charges with the negative ones of the phosphates, down to values around +20 mV below which aggregation occurs (FIG. 1D).

For further experiments, CS—Fe/AZT-TP nanoparticles were used at the critical N/P ratio of each CS—Fe type of complex, corresponding to the smallest and most monodispersed nanoparticles and the higher AZT-TP content (lowest N/P ratio). The AZT-TP amount associated to each type of nanoparticles at this N/P ratio was determined using radioactive drug. AZT-TP encapsulation efficiency was found to increase with the iron content of CS—Fe, up to around 60% for CS-$Fe_{9\%}$ and CS-$Fe_{12\%}$. In terms of drug loading, this corresponds to around 45% (calculated as AZT-TP weight on nanoparticle weight).

2. Nanoparticle Toxicity and Uptake by Macrophages

AZT-TP nanoparticles have been tested on 2 different macrophage cell lines, murine macrophages J774A.1 and human monocyte-derived THP-1 macrophages which express the CD4 receptor (Konopka et al *Aids Res. Hum. Retrovir.,* 2002, 18, 123-131). The toxicity of nanoparticles was first assessed by evaluation of the viability of cells after nanoparticle exposure by an MTT test. Results show that for nanoparticle concentrations up to 0.1 mg/mL, a cell viability of 60-80% is maintained for both cell lines and all the formulations, without any notable trend between the CS—Fe complexes used for nanoparticle formation. Therefore, this concentration has been chosen as safe towards the cells for the next studies. Furthermore, this concentration corresponds to very high amounts of AZT-TP as compared to what is commonly used for in vitro studies on HIV-infected cells. The four CS—Fe complexes in solution have been tested as well, revealing a viability around 80% without any notable trend among them (data not shown).

The effect of CS—Fe/AZT-TP nanoparticles on the AZT-TP uptake by macrophages was studied on the two cell lines after up to 8 hour exposure to various formulations prepared with radioactive AZT-TP. For J774A.1 cells, the basal AZT-TP uptake is around 3 nmol per million cells when the free molecule is exposed to cells, whereas nanoparticle-encapsulated AZT-TP is internalized up to 3 times more, the CS-$Fe_{12\%}$-based nanoparticles being the most effective ones (FIG. 2A).

Figure 2:
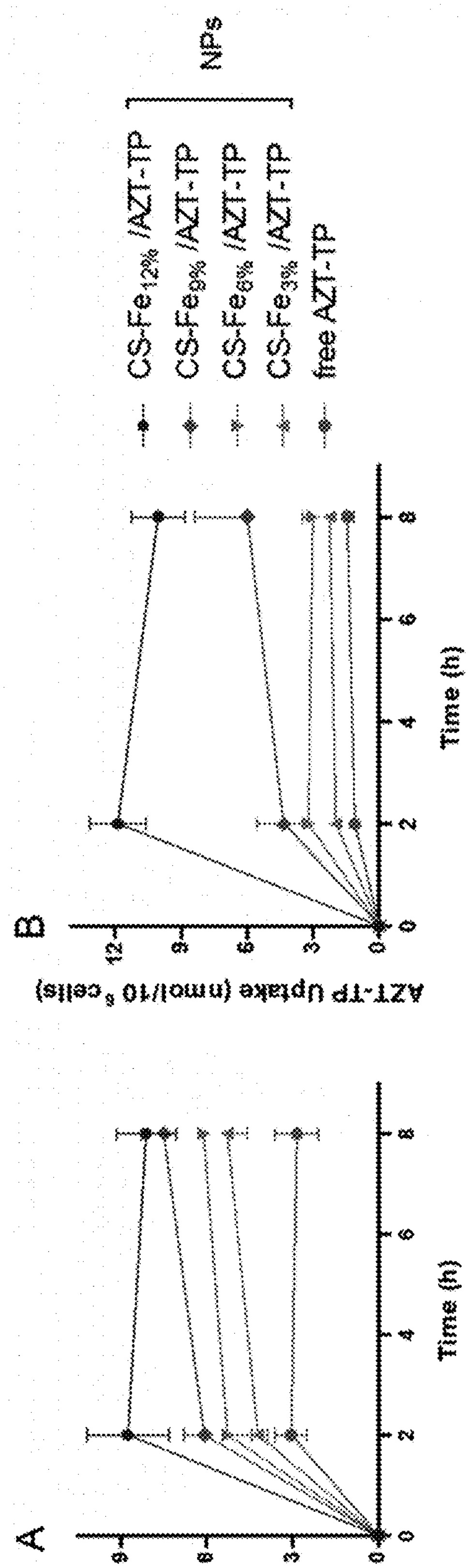
FIG. 2 shows the effect of nanoparticles on AZT-TP uptake by macrophages. [$^3$H]-AZT-TP uptake by (a) J774A.1 and (b) THP-1 macrophages after incubation with various CS—Fe/AZT-TP nanoparticles (NPs) or with free AZT-TP.

For THP-1 macrophages, in which basal AZT-TP uptake is even smaller, the effect of nanoparticles is even more pronounced, especially for CS-$Fe_{12\%}$-based nanoparticles which increased AZT-TP uptake by 5- to 6-fold compared to the free drug, reaching 12 nmol per million cells (FIG. 2B).

Considering these results, nanoparticles prepared from CS-$Fe_{12\%}$ have been selected for further investigations.

3. Inhibition of HIV-1 Infection of Primary T Cells by AZT-TP Nanoparticles

In the course of HIV-1 infection, T cells act as the major target for HIV-1 and constitute the primary reservoir for the virus. We therefore tested whether nanoparticles could limit the production of the virus by infected cells.

Because CCR5-tropic viruses are predominantly transmitted in vivo, T cells were infected for 3 h with the R5 subtype B strain BaL and further cultured either alone (non-treated) or in the presence of free AZT, CS-$Fe_{12\%}$/TPP nanoparticles (E-NP), AZT-TP or CS-$Fe_{12\%}$/AZT-TP nanoparticles (NP). The activity on HIV-infected cells has been investigated for CS-$Fe_{12\%}$/AZT-TP nanoparticles. After six days of culture, the virus production in culture supernatants was monitored with p24 ELISA, and the frequency of infected T cells was determined following the intracellular expression of p24 by flow cytometry. Treatment of HIV-1-infected T cells with nanoparticles resulted in significant inhibition of the viral replication in a dose-dependent manner. Indeed, increasing concentrations of NP inhibited the release of the virus in the supernatant of infected T cells from 24% to 95% ($p<0.05$ vs RPMI 1640 control), whereas E-NP had no antiviral activity. Interestingly, NP showed similar inhibitory activity as AZT or AZT-TP. In addition, the treatment of infected T cells with NP reduced significantly the frequency of p24+ cells to similar levels to those induced by AZT and AZT-TP ($p<0.01$ vs non-treated).

To further study the mechanism underlying NP-mediated inhibition of viral replication in this model, the capacity of NP to interfere with the process of virus entry into T cells was assessed. T cells were pre-treated with indicated molecules followed by exposure to HIV-1 for 1 h at 37° C. After washing, cell-associated HIV p24 was determined by HIV p24 ELISA. Similarly to AZT, NPs induced a small but significant decrease of virus replication into T cells ($p<0.05$ for all comparisons by reference to non-treated).

However, one may argue that NP-induced decrease of p24 levels was the consequence of T-cell death. To address this hypothesis, the cytotoxicity of the inhibitors using 7-AAD staining was tested to detect apoptotic cells. Similar frequencies of 7-$AAD^{neg}$ living cells were found in the absence or presence of the highest concentrations of each inhibitor (2 μM), indicating the lack of toxicity of NP in vitro.

Altogether these data show that nanoparticle encapsulation of AZT-TP preserved its antiviral activity while being non toxic for T cells. Considering that the capacity of NP to interfere with virus entry into T cells was not spectacular (decrease by 1.2 to 1.6 fold), it may indicate that NP act similarly to AZT by interrupting the viral cycle thus preventing new infection rather than acting at early steps of virus entry.

4. Inhibition of HIV-1 Infection of Macrophages by Nanoparticles

Figure 3:
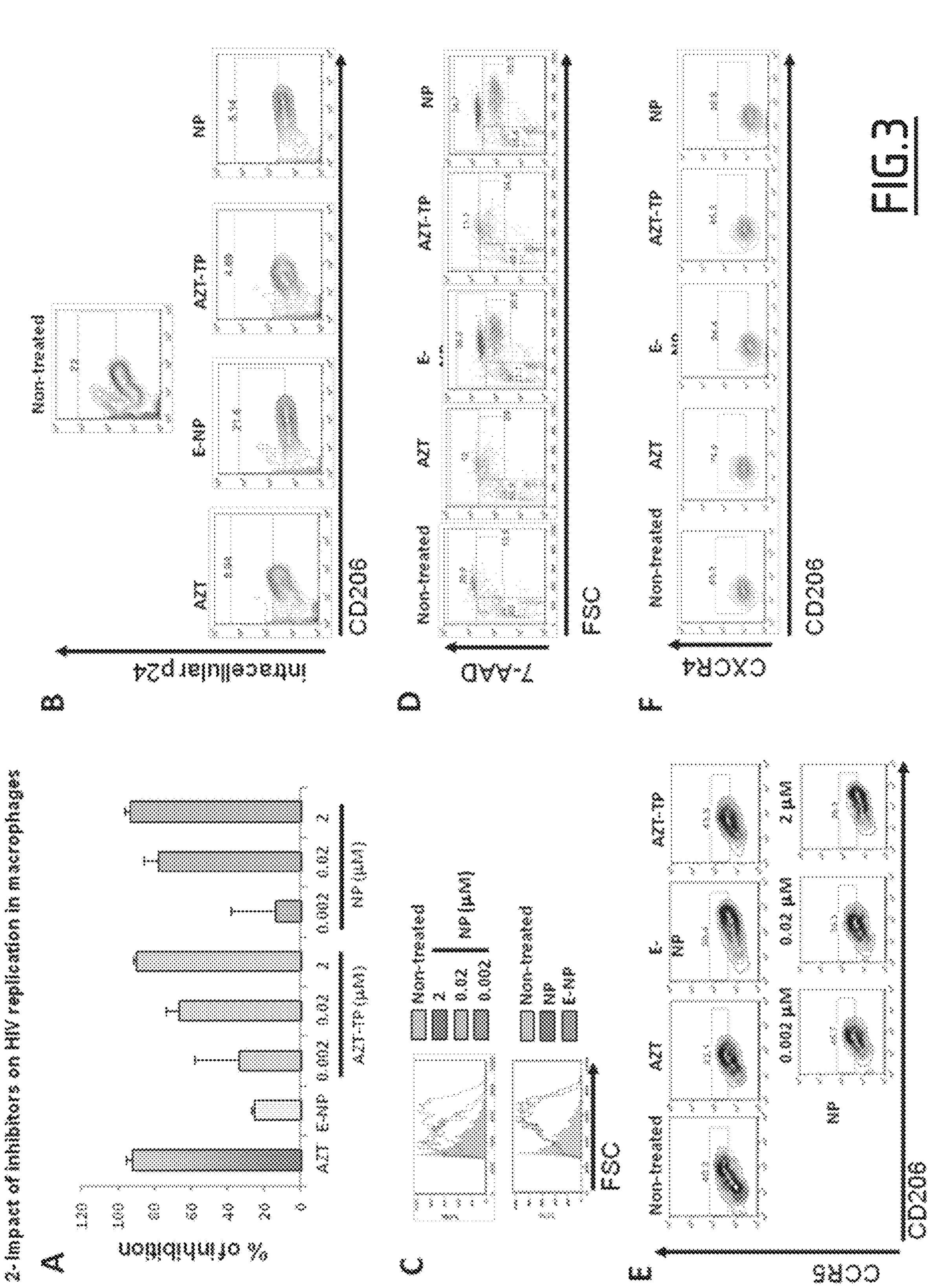
FIG. 3 represents the inhibition of HIV-1 replication in AZT-NP-treated macrophages. Monocyte-derived macrophages were infected with CCR5-tropic HIV-$1_{Ba\text{-}L}$ for 3 h. After several washes, increasing concentrations of AZT derivatives were added to infected macrophages for 6 days of culture. The level of virus replication was monitored in culture supernatants by the p24 antigen capture ELISA. The infection inhibition is expressed as percentage of the average of three independent experiments (A). The frequency of infected cells was determined by flow cytometry after a constraining of macrophages with mAbs anti-CD206 (a marker of macrophages) and mAbs anti-p24 which target intracellular HIV-1 (B). Addition of AZT derivatives was followed by the increase of the size of macrophages as assessed by the Forward-Scattered light parameter (FSC) in flow cytometry (C). To exclude any cytotoxicity of AZT compounds, treated macrophages were incubated with the 7-AAD molecule staining specifically dead cells whereas living cells remained unstained (D). Using flow cytometry, the expression of the two HIV-1 coreceptors CCR5 (E) and CXCR4 (F) was determined at the surface of AZT derivatives-treated macrophages.
Figure 4:
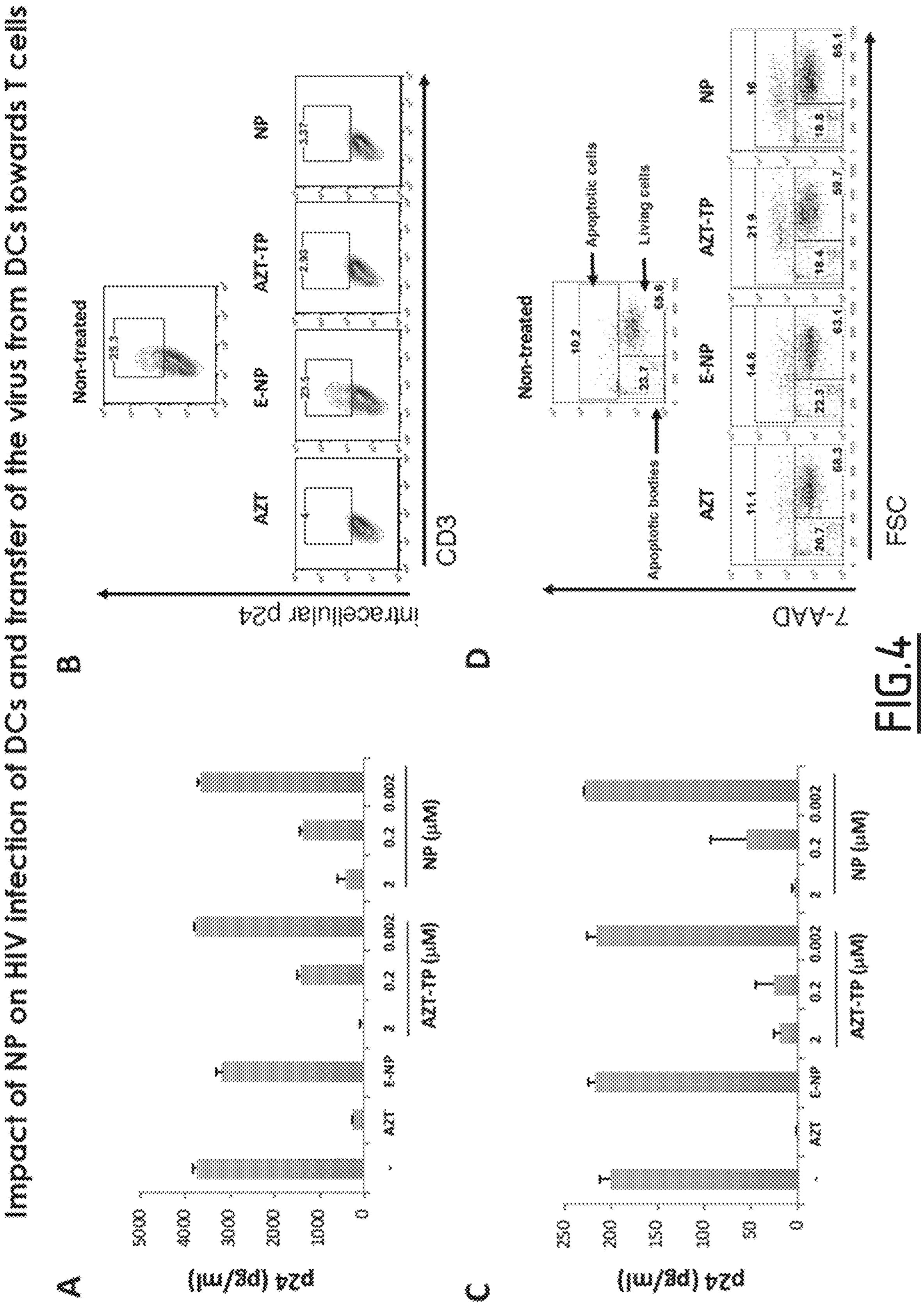
FIG. 4 shows that NP induced a decrease in viral production by DCs (A). The question of the impact of NP on HIV-1 transmission from DCs to autologous T cells was addressed. DCs were first infected with HIV-1, then incubated with increasing concentrations of AZT derivatives before T cells were added. Treatment of DCs with NP inhibited the production of HIV-1 in a dose-dependent manner, as observed with AZT and AZT-TP (A) that was associated with a lower frequency of p24+ T cells (B,C), thus suggesting that NP were able to interfere with HIV transmission from DCs to T cells, which constitutes one of the major process of virus dissemination in vivo. A possible toxic effect of NP was ruled out as shown with the 7-AAD assay (D).

Macrophages are considered as one of the major targets for HIV in vivo and a source of viral reservoir. Macrophages were infected for 3 h with HIV-1 BaL and further cultured either alone (non-treated) or in the presence of AZT derivatives. Following six days of culture, virus production was quantified in culture supernatants and the frequency of infected cells determined by flow cytometry. As illustrated in FIG. 3, NP abrogated the production of HIV-1 by macrophages in a dose-dependent manner ($p<0.05$ for NP at 0.02 and 2 μM, in comparison to RPMI 1640 control). Similarly, treatment of macrophages with AZT and AZT-TP inhibited HIV-1 production, whereas E-NP had no effect. Inhibition by AZT derivatives of viral particle release by infected macrophages was confirmed by the decreased number of p24+ cells. In addition, an efficient capture of nanoparticles by macrophages was suggested by their increased size after treatment, in a dose-dependent manner. Notably, inhibition of viral production by macrophages, observed in the presence of NP, was not related to a toxic activity of NP in vitro.

Interestingly, E-NP- or NP-treatment of macrophages decreased the expression of HIV-1 coreceptor CCR5 at their surface whereas AZT or AZT-TP treatment did not interfere with the expression of this coreceptor, suggesting that besides their AZT-dependent antiviral effect, chitosan-iron nanoparticles may interfere with viral entry by modulating cell surface expression of CCR5.

5. NP Block HIV-1 Infection of DCs and Virus Transfer from DCs to T Cells

The antiviral activity of AZT derivatives was first tested on HIV-1 infected-DCs. NP induced a decrease in viral production that was associated with a lower frequency of p24+ T cells. Next the question of the impact of NP on HIV-1 transmission from DCs to autologous T cells was addressed. In these experiments, DCs were first infected with HIV-1, then incubated with increasing concentrations of AZT derivatives before T cells were added.

Treatment of DCs with NP inhibited the production of HIV-1 in a dose-dependent manner, as observed with AZT and AZT-TP, thus suggesting that NP were able to interfere with HIV transmission from DCs to T cells, which constitutes one of the major process of virus dissemination in vivo. A possible toxic effect of NPs was ruled out with the 7-AAD assay.

6. Delivery to Lymph Nodes

The ability of CS-$Fe_{12\%}$/AZT-TP nanoparticles to improve AZT-TP accumulation in lymph nodes was investigated on mice after subcutaneous administration of nanoparticles or free AZT-TP using radioactive AZT-TP. Mice were administered the treatments by subcutaneous injection into the hock after having been anesthetized. The injection into the hock has already been shown to be a relevant model of subcutaneous administration to target the lymph nodes and reduce animal sufferance (Kamala et al *J. Immunol. Methods,* 2007, 328, 204-214).

Figure 5:
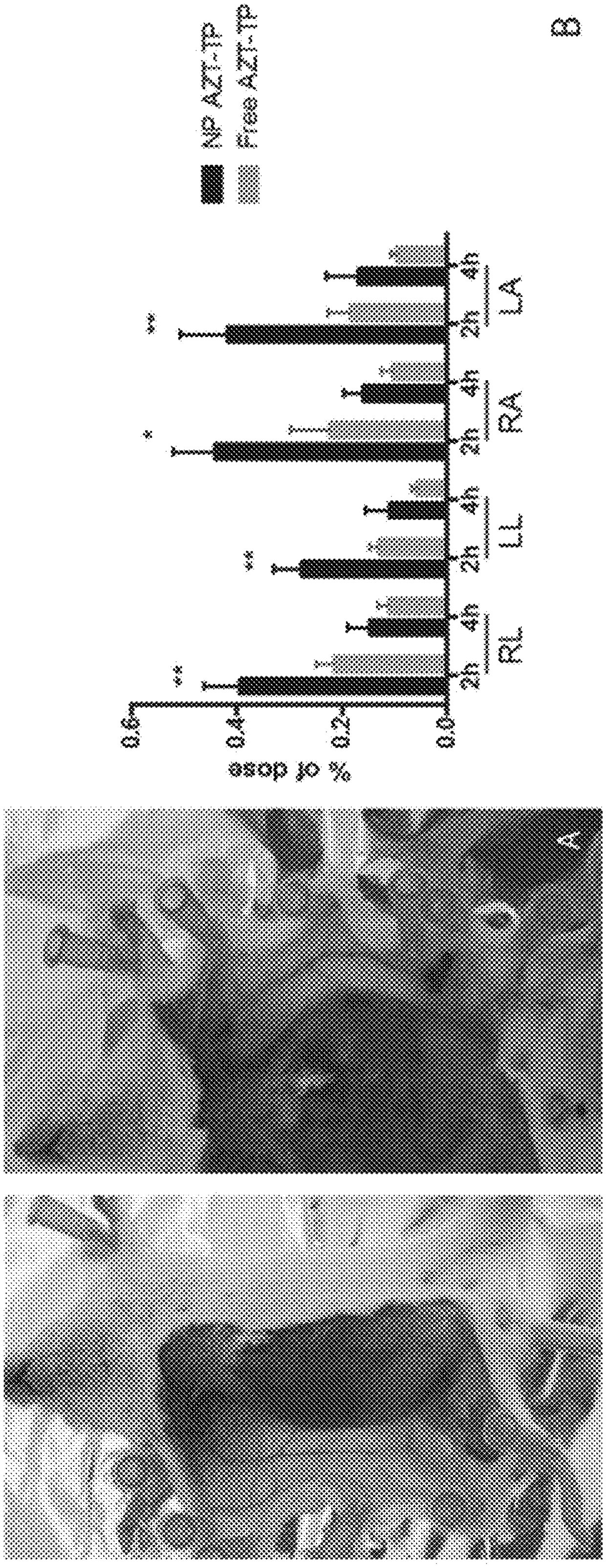
FIG. 5 illustrates the lymph node retention of [$^3$H]-AZT-TP nanoparticles after subcutaneous administration to mice. Fraction of injected dose in inguinal and axillary lymph nodes 2 and 4 hours post-injection of nanoparticle (NP) AZT-TP or free AZT-TP. RL=right leg, LL=left leg, RA=right arm, LA=left arm. % of dose is calculated as the radioactivity in the lymph node divided by the radioactivity injected. NP AZT-TP values are statistically different from Free AZT-TP values as determined by T test and two-way ANOVA. The symbols * and ** represent significant change to the level of $p<0.1$ and $p<0.05$ respectively.
Figure 6:
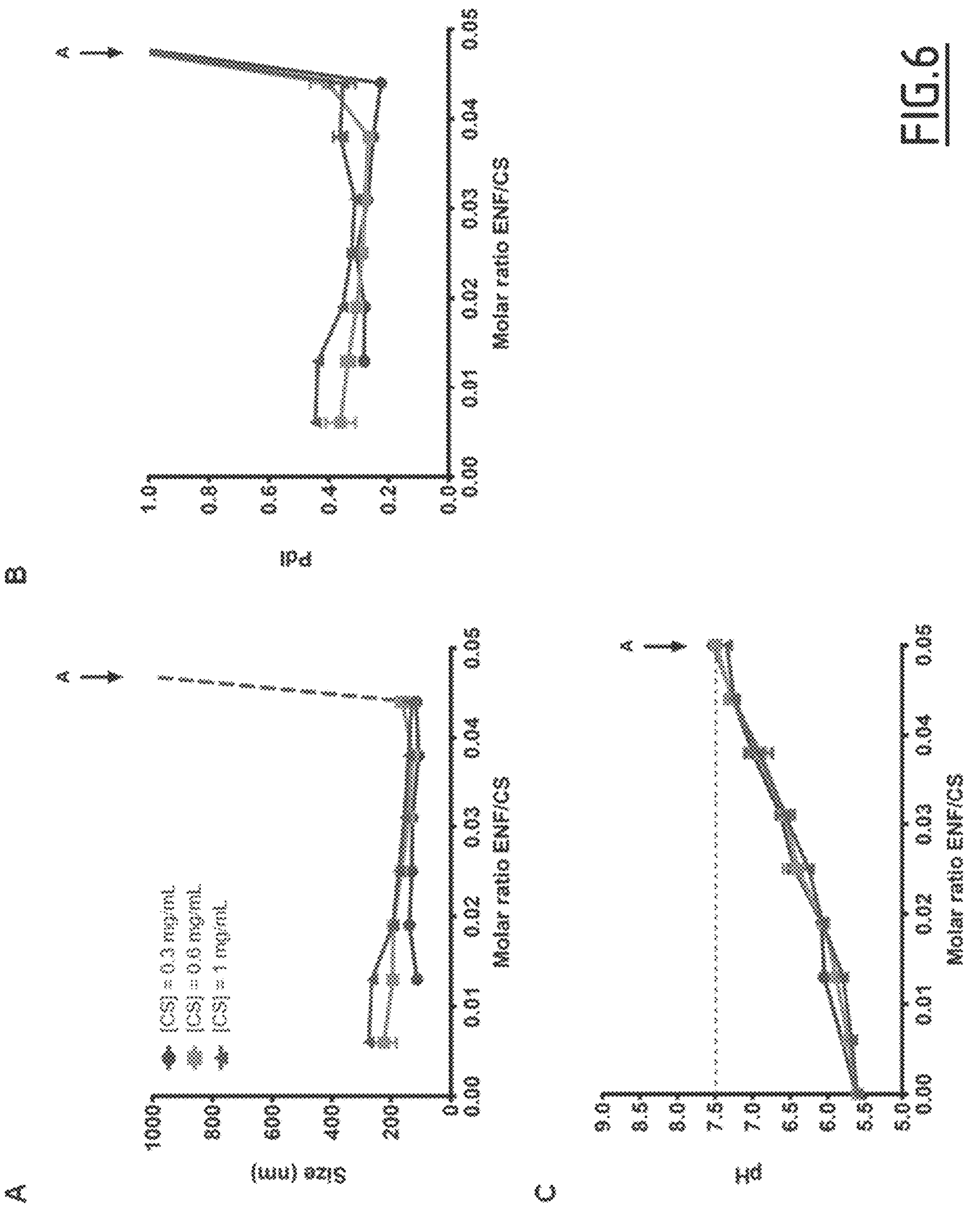
FIG. 6 illustrates the (A) Mean size, (B) polydispersity index and (C) pH of CS/ENF nanogels prepared with different concentration of CS (0.3 mg/mL (●), 0.6 mg/mL (■) and 1 mg/mL (▲)) as function of the ENF/CS molar ratio. Appearance of macroscopic aggregates is indicated by "A".
Figure 7:
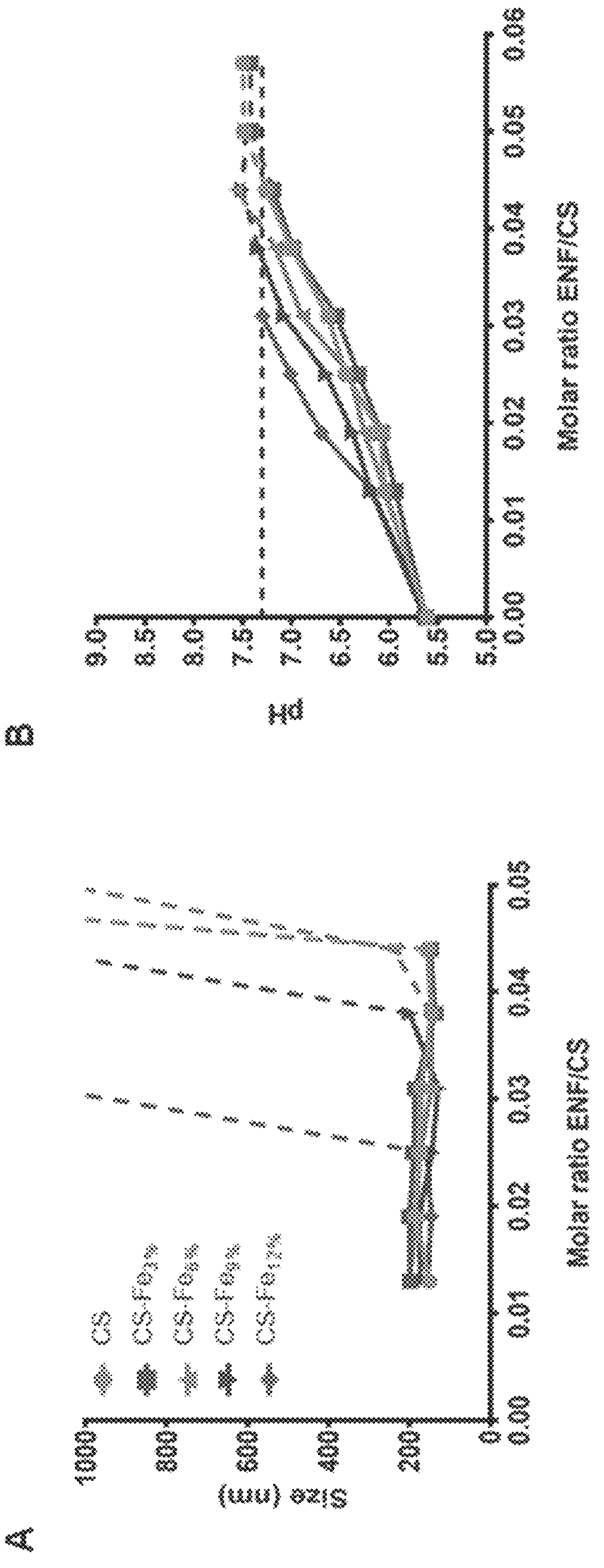
FIG. 7 illustrates (A) Mean size and (B) pH of CS—Fe/ENF composite nanogels prepared with different iron contents (0% (●), 3% (■), 6% (▲), 9% (▼), 12% (♦)) as function of the ENF/CS ratio. Appearance of macroscopic aggregates is indicated by "A".
Figure 8:
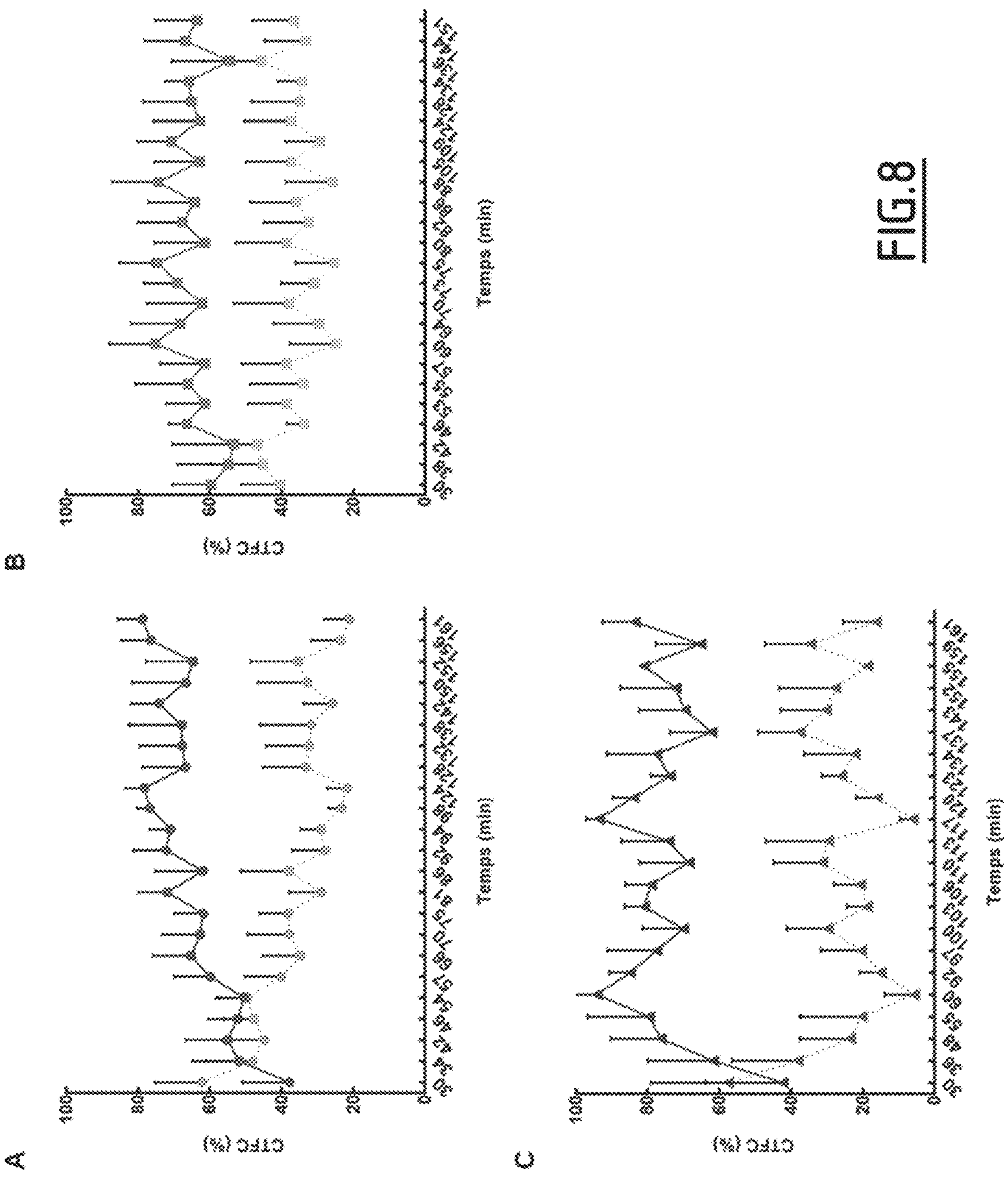
FIG. 8 shows the intracellular (——) and extracellular (....) fluorescence intensity of CS/ENF nanogels at 0.013 (■) or 0.065 (▲) ENF/CS molar ratio and Cy5.5-labeled ENF solution (●) in RAW 264.7 cells. Data are mean±SD of fluorescence intensity as function of time.
Figure 9:
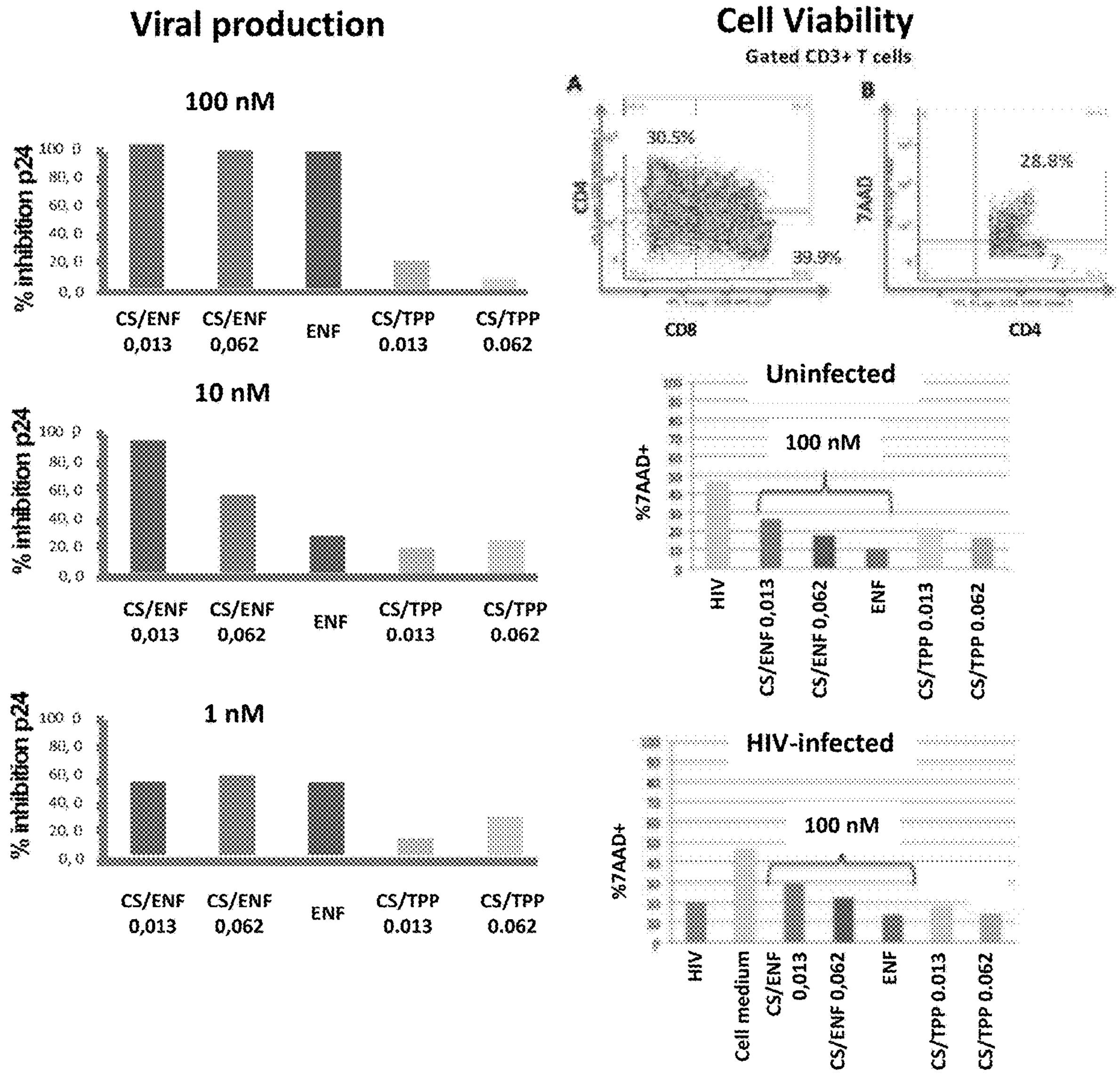
FIG. 9 illustrates the antiviral activity of CS/Enf nanoparticles on PHA-activated T cells (A) and macrophages (B) infected with HIV-1.

The exposure of lymph nodes to AZT-TP was measured by inguinal and axillary lymph nodes collection 2 and 4 hours after injection. As a control, radioactivity of non-treated mice's lymph nodes has been measured, giving results close to the blank's values. To better illustrate the lymphatic distribution, mice were injected into inguinal lymph node by trypan blue solution as described above. This method was developed to identify the hind leg lymphatic drainage of mice and to facilitate our studies of AZT-TP accumulation in the inguinal and axillary lymph nodes. Injection time was not critical, since euthanasia at any time after injection gave visible blue labeling of lymph nodes. In fact, dye uptake was detected immediately after euthanasia, indicating that there is some lymphatic drainage post mortem. Indeed, the liquid (blue) has diffused through the lymphatic duct (invisible before) and reached the axillary lymph node. Concerning the tissue distribution, two hours after the administration, the detected radioactivity was always higher in the case of nanoparticles as compared to the free molecule (FIG. 5). These levels then decrease after 4 hours, still remaining higher in the case of nanoparticles in all cases. As expected, higher levels are found in the lymph nodes closest to the injection site, which is in the right hock. These results clearly show the ability of CS-$Fe_{12\%}$/AZT-TP nanoparticles to deliver a triphosphate nucleotide analog to the lymph nodes, one of the most important viral sanctuaries.

3. Conclusions

Using novel chitosan carriers loaded with AZT-TP (NP), a drug encapsulation efficiency greater than 60% and its efficient uptake by the phagocytes were demonstrated. As compared to free AZT, non-toxic concentrations of NP showed similar anti-HIV-1 activity on T cells, macrophages and dendritic cells. Similarly to free AZT, NP blocked the transmission of the virus from DCs to T cells, a mechanism that sustains viral persistence. In vivo studies to evaluate their ability to target lymph nodes showed a double AZT-TP accumulation in the case of nanoparticles as compared to the free molecule. The physico-chemistry of the formation process let think that the principle is applicable to other drugs The delivery of AZT-TP to key sites of the infection at the cellular level (leukocytes) and tissular level (lymph nodes) was demonstrated. Nanoparticles assemble through ionic interactions between CS—Fe and AZT-TP. These systems are characterized in terms of composition, size and surface charge. In vitro studies on murine and human macrophages show that CS—Fe/AZT-TP nanoparticles induce no or low toxicity and increase the AZT-TP uptake by up to 6-fold compared to the free molecule. Furthermore, these nanoparticles retained the antiviral activity of AZT-TP, thus inhibiting HIV replication in the main targets of HIV-1 (T cells, macrophages and dendritic cells). Notably, these nanoparticles blocked the transmission of the virus from dendritic cells towards T cells, a key mechanism sustaining in vivo the viral persistence. Nanoparticles also significantly increased by 2 fold the in vivo retention of AZT-TP in lymph nodes at 2 hours after subcutaneous administration to mice. Overall, anti-microbial loaded chitosan nanoparticles appeared to be promising nanomedicines for the destruction of HIV-1 reservoirs.

Example 2: Nanoparticles of Enfuvirtide

1. Tests 1.1. Synthesis of CS—Fe Complexes

CS—Fe complexes were synthesized from chitosan (low viscosity, 83% deacetylated, Sigma) in presence of iron nitrate ($Fe(NO_3)_3$) (Sigma) in aqueous solution at various concentrations (0.1-1 M), pH and stirring times. The complex was then washed from unbound iron through precipitation with acetone and dried. A panel of CS—Fe complexes were obtained with different iron contents (2 to 20% w/w).

1.2. Characterization of CS—Fe Complexes

After hydrolysis of CS—Fe complexes using concentrated nitric acid at 200° C., the association of iron to CS was monitored by inductively coupled plasma-optical emission spectrometry (ICP-OES) and also determined by a phenanthroline-based assay (the obtained iron solution formed a complex with phenanthroline, which was then quantified through absorbance at $\lambda$=510 nm). FT-IR spectra of CS and CS—Fe complexes were acquired using a Spectrum Two FT-IR Spectrometer (Perkin Elmer) with a Diamond ATR accessory, between 4000 and 400 $cm^{-1}$.

1.3. Preparation of Nanogels ENF/CS and Composite Nanogels ENF/CS—Fe

CS solution at a final concentration (0.3-1 mg/mL) was obtained by dissolution of chitosan in an acetic acid aqueous solution between 0.525 and 1.75 mg/mL. CS—Fe solutions with different iron content were obtained by physical mixture of CS and CS-$Fe_{18\%}$ solutions (1:0.25, 1:0.5, 1:1 or 1:2) at 0.3 mg/mL. The pH of the solutions was adjusted between 5.6 and 6.2 with 1 M NaOH (pH-meter SevenMulti®, Mettler Toledo). Enfuvirtide (Proteogenix) was solubilized in 10 mM $Na_2CO_3$ or 25 mM NaOH at 5 mg/mL. To avoid freeze-thaw cycles, the peptide solution was separated into aliquot and storage at −20° C.

For the study of the nanogel formation domains, increasing amounts of Enfuvirtide, from 0.02 to 0.2 mL, were added dropwise to 1 mL of CS or CS—Fe solution under magnetic stirring. The nanogel formation domains are expressed as a function of the molar ratio between Enfuvirtide and amine group of chitosan (ENF/CS). For fluorescence studies, the nanogels were formed from a 5 mg/mL Enfuvirtide solution containing Cy5.5-labeled Enfuvirtide as a tracer (10% w/w).

For the storage purposes, the nanogels were freeze-dried by adding trehalose as cryoprotectant to a 1 mL suspension at the final concentration of 10% w/v. The resulting suspension was frozen in liquid nitrogen and freeze-dried at −80° C. and P<1 mbar for 24 hours using a Chris Alpha 2-4 LD Plus.

1.4. Nanogel Characterization

The mean size, the polydispersity index (PdI) and the zeta potential of nanogels were determined by dynamic light scattering (DLS) using a Zetasizer Nano ZS (Malvern Instrument, UK) with a 173° scattering angle at 25° C. on undiluted nanogel suspensions. The measurement position and attenuator values were automatically selected. The results were represented as the size distribution by intensity percentage.

1.5. Encapsulation Yield and Drug Loading of Nanogels

Nanogels were prepared as described above from CS—Fe complexes containing 0-12% w/w Fe at 0.3 mg/mL and pH=5.6. Nanogels were purified by ultracentrifugation (40 000 rpm, 2 h at 4° C.). The supernatant was withdrawn, whereas the pellet was dissociated by addition of a saline solution (1 M NaCl) under magnetic stirring overnight at 4° C.

The peptide content of the supernatant and the pellet was determined using the bicinchoninic acid (BCA) assays (Pierce™ BCA Protein Assay Kit, Thermo Fisher). Prior to beginning the assay, BCA reagent was prepared by mixing BCA solution with a 4% cupric sulfate solution (50:1). Samples (0.1 mL) were combined with BCA reagent (2 mL) and heated for 30 min at 60° C. Samples were cooled to room temperature then the absorbance at 562 nm was determined with UV-Vis spectroscopy (Lambda 25 Systems, PerkinElmer). The obtained results allowed to determine the encapsulation yield and the drug loading as the amount of peptide associated to nanogels for 100 mg of nanogels.

$$\text{Encapsulation yield } (\%) = 100 \times \frac{ENF_{initial}(\text{mg}) - ENF_{dosed}(\text{mg})}{ENF_{initial}(\text{mg})}$$

$$\text{Drug loading } (\%\ w/w) = 100 \times \frac{ENF_{initial}(\text{mg}) - ENF_{dosed}(\text{mg})}{(ENF_{initial}(\text{mg}) - ENF_{dosed}(\text{mg})) + CS\ \text{polymer (mg)}}$$

1.6. Colloidal Stability to Ionic Strength

The resistance of nanogels to ionic strength at pH=7 was evaluated by following the relative intensity of scattered light by dynamic light scattering (DLS) in 150 mM NaCl. DLS measurements were performed immediately after a single addition of NaCl.

Data are represented as the size distribution by intensity corrected by the average light intensity (derived count rate).

1.7. Cell Culture and Viability Assessment

RAW 264.7 mouse macrophages (from ATCC® TIB-71™) was grown in Dulbecco's Modified Eagle's Medium (DMEM) supplemented with 10% v/v fetal bovine serum (Lonza), penicillin (50 UI/mL) and streptomycin (50 µg/mL) (Sigma). Cells were maintained in a humidified incubator with 95% air/5% $CO_2$ at 37° C. and used from passage 3 to 20 after thawing.

The cytotoxicity of nanogels was determined using an MTT assay. Cells were counted with KOVA Slide and diluted to needed concentration, to be seeded in a 96-well plate at a density of 10,000 cells/mL. They were pre-incubated for 24 hours. Nanogels were prepared and diluted at different concentrations in cell culture medium and incubated with cell for 72 hours. After 72 hours, supernatants were withdrawn and a 5 mg/mL MTT solution was added. After 1 hour incubation, MTT solution was removed and DMSO was added to dissolve formazan crystals. Plates were stirred few minutes and absorbance were measured at λ=570 nm.

1.8. Cellular Uptake of Nanogels

RAW 264.7 cells were seeded on coverslips previously placed in 6-well plates at 80,000 cells/mL density in 1 mL medium per well, and pre-incubated for 24 hours. Cell membranes were stained with a primary conjugated antibody: Alexa Fluor® 488 anti-mouse F4/80 antibody (BioLegend Cat No: 123120). Briefly, cells were rinsed with phosphate-buffered saline (PBS) and then covered with a blocking buffer (1% w/v BSA in PBS) for 30 min at 37° C. to minimize the non-specific adsorption of the antibodies to the coverslip. The blocking buffer was removed, and the primary antibody diluted to 2.5 µg/mL in blocking buffer was incubated for 1 hour at room temperature in a humidified chamber.

Nanogels and the control solution were diluted 1:10 in cell culture medium and incubated with the stained cells. Nanogels were prepared using fluorescent Cy5.5-labeled Enfuvirtide as a tracer, and a free fluorescent Cy5.5-labeled Enfuvirtide solution was prepared as a control using the same fluorophore concentration. The cellular uptake of nanogels was imaged during 3 hours using an inverted confocal laser scanning microscope LSM 510 Meta (Carl Zeiss, Germany) using a Plan-Apochromat 63×/1.4 objective lens, equipped with an argon (488 nm excitation wavelength) and a helium neon laser (633 nm excitation wavelength). The green and the red fluorescence emissions were collected with a 505-635 nm band-pass and a 650 nm long pass emission filter respectively, under a sequential mode. The pinhole was set at 1.0 Airy unit. 16 bit numerical images were acquired with LSM 510 software version 3.2. During imaging cells were maintained in healthy state at a temperature of 37° C. in AttoFluor® cell chamber (Invitrogen).

The microscopy images were analyzed with ImageJ. Intracellular and extracellular compartments of each imaged cell were defined with the anti-F4/80-Alexa Fluor 488 antibody staining. Corrected total cell fluorescence (CTFC) of nanogels was determined by image analysis. Results are expressed as mean±SD.

2. Results 2.1. Preparation of CS—Fe Complexes

All CS—Fe complexes synthesized present similar FT-IR spectra. The —OH and —NH characteristic bands of the glucosamine units are no longer visible in the CS—Fe complexes due to the interaction with iron. CS—Fe complexes with iron/glucosamine molar ratios ([M]/[L]) between 0.1 and 0.5 were obtained, corresponding to an iron content of 2 to 20% w/w. The maximum iron content is consistent with the CS—Fe complex structure proposed in the literature: each iron atom binds to two glucosamine units ([M]/[L]=0.5).

By increasing $Fe(NO_3)_3$ concentration, the iron incorporation in CS—Fe complexes was found to decrease, which was attributed to a decrease in pH. Coordination complexes between chitosan and iron require $NH_2$ groups, which are less available at acidic pH due to the chitosan protonation.

2.2. Formation of Nanogels and Characterization 2.2.1. Impact of pH

The nanogel formation domains have been investigated at different initial pH of chitosan solution ($pH_{initial}$)=5.6-5.8-6.0-6.2 at [CS]=0.3 mg/mL, expressed as a function of the molar ratio between Enfuvirtide and amine group of CS (ENF/CS): The critical ratio decreases for increasing the $pH_{initial}$ and the peptide loading decreases with the critical ratio. The pH of the resulting nanogel suspensions increases in function of molar ratio ENF/CS until a pH value of 7.3 corresponding to the critical ratio. The aggregation behavior is observed from a pH value>7.3.

TABLE 1

Nanogel characteristics for different initial pH of CS solution at critical ENF/CS ratios.

| pH | 5.6 | 5.8 | 6.0 | 6.2 |
|---|---|---|---|---|
| Critical molar ratio ENF/CS | 0.044 | 0.038 | 0.031 | 0.019 |
| Size (nm) | 155 ± 16 | 173 ± 40 | 175 ± 46 | 316 ± 117 |
| Poly-dispersity | 0.225 ± 0.018 | 0.292 ± 0.063 | 0.269 ± 0.025 | 0.274 ± 0.002 |
| pH | 7.26 ± 0.09 | 7.41 ± 0.21 | 7.24 ± 0.23 | 7.27 ± 0.11 |

2.2.4. Loading Efficiency and Drug Loading of Nanogels

The determination of maximal drug loading and encapsulation yield of nanogels were determined in buffered ($Na_2CO_3$) and non-buffered (NaOH) medium by BCA assay: The association of Enfuvirtide increases with increasing ENF/CS molar ratios until the critical ratio.

TABLE 2

Nanogel characteristics in function of the medium ($Na_2CO_3$ or NaOH) at ENF/CS critical ratios.

| Medium | NaOH | $Na_2CO_3$ |
|---|---|---|
| Critical molar ratio | 0.044 | 0.062 |
| Size (nm) | 155 ± 16 | 155 ± 7 |
| Polydispersity | 0.225 ± 0.018 | 0.133 ± 0.012 |
| pH | 7.26 ± 0.09 | 6.87 ± 0.14 |
| Encapsulation yield (%) | 78.8 ± 11.4 | 86.2 ± 2.8 |
| Drug loading (% w/w) | 49.9 ± 4.6 | 58.9 ± 0.8 |

2.2.5. Impact of Polymer: CS or CS—Fe Complexes

The formation domains of composite nanogels with different iron content of CS-$Fe_{18\%}$ have been investigated at [CS]=0.3 mg/mL and $pH_{initial}$=5.6:

The critical ratio decreases for increasing the iron content, and the peptide loading decreases with the critical ratio. The pH of the resulting nanogel suspensions increases with the molar ratio ENF/CS and the variation of pH values is faster when the iron content increases.

TABLE 3

Nanogel characteristics in function of iron content at critical ENF/CS ratios.

| Iron content | 0% | 3% | 6% | 9% | 12% |
|---|---|---|---|---|---|
| Critical molar ratio | 0.044 | 0.044 | 0.038 | 0.031 | 0.025 |
| Size (nm) | 155 ± 16 | 148 ± 21 nm | 146 ± 21 nm | 130 ± 3 nm | 156 ± 7 nm |
| Polydispersity | 0.225 ± 0.018 | | | | |
| pH | 7.26 ± 0.09 | 7.19 ± 0.20 | 7.16 ± 0.11 | 7.07 ± 0.08 | 7.30 ± 0.09 |

In the following experiments, the $pH_{initial}$ of chitosan solution was fixed at 5.6.

2.2.2. Impact of Chitosan Concentration

The nanogel formation domains have been also investigated at different chitosan concentration (0.3-1 mg/mL), at $pH_{solution}$=5.6:

For the different concentrations of chitosan, the same nanogel size and PdI are obtained and the evolution of the pH values was similar. The chitosan concentration has no impact on nanogel size and critical molar ratio ENF/CS.

2.2.3. Impact of Enfuvirtide Buffer

The nanogel formation domains have been investigated with Enfuvirtide solubilized in buffered (10 mM $Na_2CO_3$) or non-buffered medium (25 mM NaOH) at [CS]=0.3 mg/mL and $pH_{initial}$=5.6:

The aggregation behavior is always observed from a pH value>7.3 and the critical ratio increases in function of the formation medium. The buffered medium limits the pH increase and allows more enfuvirtide to be loaded in CS/ENF nanogels.

The positive surface charge of nanogels decreases from +30 mV to +5 mV with increasing ENF/CS molar ratios until the critical ratio.

The impact of different studied parameters on the nanogel formation domains is summarized in Table 4.

TABLE 4

Effect of formulation parameters on nanogel characteristics (size, surface charge and drug loading).

| Parameters | Nanogel size | Surface charge | Drug loading |
|---|---|---|---|
| Molar ratio ENF/CS | ≈ | ↘↘ | ↗↗ |
| $pH_{initial}$ of CS | = | = | ↗↗ |
| [CS] | = | = | ↗ |
| Enfuvirtide buffer | = | = | = |
| Iron content of CS—Fe | = | = | ↘ |

2.3. Nanogel Resistance to Ionic Strength

The resistance of CS/ENF and CS—Fe/ENF nanogels to ionic strength at pH=7 was evaluated at critical ratio by following the relative intensity of scattered light by DLS in 150 mM NaCl.

Increasing the iron content of CS/ENF nanogels increases their sensitivity to 150 mM NaCl suggesting the effective role of iron in the decreased stability of CS/ENF nanogels.

2.4. In Vitro Studies 4 nanogel formulations with different physico-chemical properties were selected for the biological evaluation:

TABLE 5

| Selected nanogel characteristics | | | | |
|---|---|---|---|---|
| | CS/ENF nanogels | | CS—Fe/ENF nanogels | |
| Molar ratio ENF/CS | 0.013 | 0.065 | 0.013 | 0.037 |
| Iron content (% w/w) | 0 | 0 | 9 | 9 |
| Size (nm) | 258 ± 1 | 156 ± 0 | 162 ± 1 | 142 ± 0 |
| Zeta potential (mV) | 29.9 ± 1.1 | 6.3 ± 0.1 | 27.0 ± 0.5 | 6.3 ± 0.1 |
| Drug loading (% w/w) | 19.8 ± 2.5 | 58.9 ± 0.6 | 21.4 ± 5.4 | 55.3 ± 2.5 |
| Encapsulation yield (%) | 74.5 ± 11.4 | 86.2 ± 2.8 | 82.3 ± 26.2 | 93.1 ± 9.2 |

2.4.1. Cell Viability Evaluation

Cytotoxicity tests were realized after 72 h incubation of the 4 selected nanogel formulations on RAW 264.7 mouse macrophages (n=3):

Nanogels do not show toxicity for concentrations up to 30 μg/mL for all nanogels formulations.

2.4.2. Cellular Uptake Kinetics of Nanogels

Cell uptake kinetic of nanogels using Cy5.5-labeled Enfuvirtide was monitored by confocal microscopy.

The fluorescence intensity measurements showed that the cell uptake is influenced by the size and the surface charge of the nanogels. The intracellular fluorescence is higher with the small and neutrally charged nanogels (ENF/CS molar ratio=0.065) than the large and positively charged nanogels (ENF/CS molar ratio=0.013).

3. Conclusions

Chitosan-based, enfuvirtide-loaded nanogels were developed with a high drug loading (up to 58% w/w) and with an efficiency yield (around 80%). The incorporation of iron allows a modulation of the nanogel stability. The tuning of CS/Enf ratios allows a modulation of the size and the surface charge of nanogels, which in turn allows a control of the cellular delivery of enfuvirtide.

| Antiviral drug | AZT-TP | | Enfuvirtide | |
|---|---|---|---|---|
| Nanogel type | CS | CS—$Fe_{12\%}$ | CS | CS—$Fe_{9\%}$ |
| Drug encapsulation | | | | |
| Max. drug/CS (mol drug/mol N) ratio | 0.304 | 0.274 | 0.062 | 0.037 |
| Max. drug/CS w/w ratio | 0.920 | 0.828 | 1.667 | 1.000 |
| Max. −/+ charge ratio[1] | 2.20 | 1.98 | 0.60 | 0.36 |

-continued

| Antiviral drug | AZT-TP | | Enfuvirtide | |
|---|---|---|---|---|
| Nanogel type | CS | CS—$Fe_{12\%}$ | CS | CS—$Fe_{9\%}$ |
| Max. drug loading (content) of nanogels (% w/w) | 43.7 | 45.0 | 58.9 | 55.3 |

[1]Calculated at pH = 7 using an ionization ratio of glucosamine residues of 0.5

| | | | | |
|---|---|---|---|---|
| Stability in 150 mM NaCl[2] | 2% | 63% | 81% | 42% |
| Cell uptake[3] | 3 nmol/$10^6$ cell | 9 nmol/$10^6$ cells | Modulation of membrane/cytosol delivery | n/d |
| Antiviral activity | n/d | Similar to free drug | Slightly enhanced for Enf/CS = 0.013 compared to free drug | To be confirmed |

[2]Evaluated as turbidity ratio compared with deionized water. Values shown for AZT-TP were determined using ATP as model drug.
[3]In vitro drug uptake by macrophages using radioactive [$^3$H]-AZT-TP or Cy5.5 fluorescent derivatives enfuvirtide

The invention claimed is:

1. A method for treating HIV and/or the symptoms thereof comprising administering to a subject in need thereof, by the sub-cutaneous route, a therapeutically effective amount of a nanoparticle comprising AZT-TP encapsulated by an encapsulation complex in the form of a chitosan nanogel, wherein the encapsulation complex comprises chitosan and $Fe^{3+}$, and wherein the chitosan/$Fe^{3+}$ complex comprises between 9 and 12% iron based on total weight of the chitosan/$Fe^{3+}$ complex, and wherein the content of AZT-TP is between 40 and 50% in weight with respect to the total weight of the nanoparticle, wherein the nanoparticle is characterized in that, following subcutaneous administration, the fraction of injected dose of AZT-TP in inguinal and axillary lymph nodes at 2 hours post-injection is at least 2-fold higher than an equal dose of free AZT-TP.

2. The method according to claim 1 wherein the administration comprises administering said nanoparticle in an aqueous suspension.

3. The method according to claim 1, wherein the nanoparticle is characterized in that, in an in vitro uptake assay using human THP-1 macrophages, AZT-TP uptake from the nanoparticle is increased by at least 5-fold relative to free AZT-TP.

4. The method according to claim 1, wherein the nanoparticle has a mean diameter of about 150 nm.

5. The method according to claim 1, wherein the chitosan/$Fe^{3+}$ complex comprises 12% iron based on total weight of the chitosan/$Fe^{3+}$ complex, and wherein the content of AZT-TP is about 45% in weight with respect to the total weight of the nanoparticle.

* * * * *